US008969092B2

(12) United States Patent
Obata et al.

(10) Patent No.: US 8,969,092 B2
(45) Date of Patent: Mar. 3, 2015

(54) GEL PARTICLE MEASUREMENT REAGENT AND MEASUREMENT METHOD USING SAME

(75) Inventors: Toru Obata, Tokyo (JP); Masakazu Tsuchiya, Mount Pleasant, SC (US)

(73) Assignee: Toru Obata, Tokyo (JP)

( * ) Notice: Subject to any disclaimer, the term of this patent is extended or adjusted under 35 U.S.C. 154(b) by 0 days.

(21) Appl. No.: 13/879,965

(22) PCT Filed: Oct. 18, 2011

(86) PCT No.: PCT/JP2011/073945
§ 371 (c)(1), (2), (4) Date: Apr. 17, 2013

(87) PCT Pub. No.: WO2012/053515
PCT Pub. Date: Apr. 26, 2012

(65) Prior Publication Data

US 2013/0203177 A1 Aug. 8, 2013

(30) Foreign Application Priority Data

Oct. 18, 2010 (JP) ................................ 2010-234074

(51) Int. Cl.
*G01N 33/00* (2006.01)
*G01N 30/00* (2006.01)
*G01N 21/82* (2006.01)
*G01N 33/579* (2006.01)

(52) U.S. Cl.
CPC ................ *G01N 30/00* (2013.01); *G01N 21/82* (2013.01); *G01N 33/579* (2013.01); *G01N 2021/825* (2013.01)
USPC ................................. 436/94; 436/93; 436/91

(58) Field of Classification Search
CPC ...................................................... G01N 33/00
USPC ............................................... 436/94, 93, 91
See application file for complete search history.

(56) References Cited

U.S. PATENT DOCUMENTS

| | | | |
|---|---|---|---|
| 5,637,474 | A | 6/1997 | Takaoka et al. |
| 2011/0013185 | A1 | 1/2011 | Obata |

FOREIGN PATENT DOCUMENTS

| | | | | |
|---|---|---|---|---|
| EP | 0 552 965 A1 | 7/1993 | | |
| EP | 2 081 024 A1 | 7/2009 | | |
| JP | 08211063 H | 8/1996 | | |
| JP | 2817606 B2 | 10/1998 | | |
| JP | 3106839 B2 | 11/2000 | | |
| JP | 3327076 B2 | 9/2002 | | |
| JP | 2010-085276 A | 4/2010 | | |
| JP | 2010-190801 A | 9/2010 | | |
| WO | WO-95/14932 * | 6/1995 | .......... | G01N 33/579 |
| WO | WO 2008/038329 A1 | 4/2008 | | |
| WO | WO 2008/139544 A1 | 11/2008 | | |
| WO | WO 2009/116633 A1 | 9/2009 | | |
| WO | WO 2010/038628 A1 | 4/2010 | | |
| WO | WO 2010/095718 A1 | 8/2010 | | |

OTHER PUBLICATIONS

English Translation of WO 1995/14932 Description. Oda et al., Method of Assaying Limulus Reagent-Reactive Substance, obtained on Sep. 4, 2013, pp. 1-4.*

International Search Report for PCT/JP2011/073945 dated Jan. 10, 2012.

Obata et al., "The study of endotoxin assay-Turbidmetric Assay or ESP Assay-", vol. 12, No. 1, pp. 97-101, Oct. 31, 2008, Japan Journal of Critical Care for Endotoxemia.

Tsuchiya et al., "Development of an endotoxin-specific Limulus amebocyte lysate test blocking β-glucan-mediated pathway by carboxymethylated curdlan and its application", vol. 45, No. 6, pp. 903-911, Nov. 1990, Japanese Journal of Bacteriology.

European Search Report issued in European Patent Application No. 11 83 4354 on Feb. 27, 2014.

Kambayashi et al., "A Novel Endotoxin-Specific Assay by Turbidimetry with Limulus Amoebocyte Lysate Containing β-Glucan", Journal of Biochemical and Biophysical Methods, vol. 22, (1991) pp. 93-100.

Tsuji et al., "Use of Magnesium to Increase Sensitivity of Limulus Amoebocyte Lysate for Detection of Endotoxin", Applied and Environmental Microbiology, vol. 45, No. 4 (1983) pp. 1342-1350.

* cited by examiner

*Primary Examiner* — Christine T Mui
(74) *Attorney, Agent, or Firm* — Birch, Stewart, Kolasch & Birch, LLP

(57) ABSTRACT

Provided is a gel particle measurement reagent effective in quickly measuring a time point of initiation of production of gel particles. A gel particle measurement reagent R is a gel particle measurement reagent to be used to be agitated continuously with a sample S containing a target substance St as a measuring object to turn the target substance St into gel particles, including: a reagent base material 1 that undergoes a gelation reaction with the target substance St; and a biologically inactive particle formation accelerating factor 2 that is added to the reagent base material, has solubility in the sample S and dissolves therein at a concentration of 0.002 to 1%, and accelerates production of gel particles G whose particle sizes are centered in a predetermined range.

11 Claims, 28 Drawing Sheets

EXAMPLE OF DETECTION OF GEL PARTICLES
BY BACKSCATTERING PHOTOMETRY

CALIBRATION CURVE

FIRST EMBODIMENT

FIRST COMPARATIVE EMBODIMENT

SECOND COMPARATIVE EMBODIMENT

EXAMPLE OF DETECTION OF GEL PARTICLES BY TRANSMISSION PHOTOMETRY

CALIBRATION CURVE

PLASMA CONCENTRATION 0.2%

PLASMA CONCENTRATION 0.1%

PLASMA CONCENTRATION 0%

PLASMA CONCENTRATION 10%

PLASMA CONCENTRATION 5%

PLASMA CONCENTRATION 1%

PLASMA CONCENTRATION 0.5%

DA 0.02%

DA 0.01%

DA 0.001%

DA 0.0001%
DISCRETE VALUE
1000
0
PARTICLE SIZE
1
32
TIME
0min
90
3.0e5
0.0e0
0min
90min
120%
0%
-20%
(S) :
(M) :
(L) :

OBSERVATION OF NEGATIVE STAINING OF DENATURED ALBUMIN

PROPER AMOUNT
OF DENATURED ALBUMIN

EXCESSIVELY LARGE AMOUNT
OF DENATURED ALBUMIN

EXCESSIVELY SMALL AMOUNT
OF DENATURED ALBUMIN

GEL PARTICLE MEASUREMENT REAGENT AND MEASUREMENT METHOD USING SAME

TECHNICAL FIELD

The present invention relates to a gel particle measurement reagent to be used for turning a target substance such as an endotoxin or β-D-glucan in a sample as a measuring object into gel particles through a gelation reaction under agitating condition, in particular, a gel particle measurement reagent intended to quickly measure a time point at which gel particles start to appear and a measurement method using the reagent.

BACKGROUND ART

A so-called endotoxin (intracellular toxin) is a major component of cell membranes of bacteria that are not stained by Gram staining (Gram-negative), and contains a lipid-polysaccharide called a lipopolysaccharide, specifically a lipopolysaccharide (LPS) in which a lipid called Lipid A and a polysaccharide chain are bound via 2-keto-3-deoxyoctonate (KDO). A lipid structural component called Lipid A included in the lipopolysaccharide, when entering a human body by infection, binds to a cellular receptor, causing inflammation, and causing a variety of severe clinical symptoms in many cases. As described above, the endotoxin is a substance causing clinical symptoms such as sepsis and bacteremia that are very high in fatality. Thus, estimation of the endotoxin which has entered the body is highly demanded clinically.

In addition, it is important that a medicinal product (such as an injection), a blood preparation, a medical device (such as an angiocatheter), a large amount of purified water, or the like is not contaminated with the endotoxin (pyrogen-free). Moreover, it is essential to properly remove or control the endotoxin in a medicinal product (such as a recombinant protein or DNA used for a gene therapy), a food addictive, a cosmetic, or the like prepared by using bacteria.

In confirmation of the removal of the endotoxin or measurement of the endotoxin in emergency medicine, promptness is required for attaining the purposes of coping with a large number of measuring samples and carrying out life-saving treatment.

Research has been made since old days on measuring an endotoxin value for treating sepsis or the like. Since the discovery of the phenomenon that a group of factors contained in a limulus amebocyte lysate each specifically react with the endotoxin, resulting in an aggregate which covers a wound, trials for quantifying the endotoxin have been made by using the limulus amebocyte lysate (LAL reagent or limulus reagent).

A first measurement method involving using the limulus reagent was a semiquantitative measurement method called a so-called gelation method, in which plasma from a patient serving as a sample is mixed with the limulus reagent, the mixture is left to stand still, the mixture is positioned upside down after a certain time, the presence or absence of gelation is confirmed by whether or not the solution is solidified, and the amount of an endotoxin is estimated based on the maximum dilution ratio at which the gelation is caused.

After that, attention has been paid to an increase in turbidity in the course of a gelation reaction. As a result, there is known a turbidimetric time assay, in which a turbidimeter using an optical measurement method is used to quantitatively measure an endotoxin concentration based on a change in turbidity involved in a gelation reaction of a mixing solution left to stand still.

In addition, a synthetic chromogenic substrate method has already been known, in which a gelation reaction causing conversion from coagulogen to coagulin is replaced by a chromogenic reaction of a synthetic substrate in the final stage of a reaction process with a limulus reagent. This method is a method in which a synthetic chromogenic substrate (Boc-Leu-Gly-Arg-p-nitroanilide) is added in place of a coagulation precursor (coagulogen) in a coagulation process, hydrolysis of the synthetic chromogenic substrate then produces free p-nitroaniline, and colorimetric analysis of the resultant yellow chromogenic development is performed to measure a coagulogen decomposition ability, thereby measuring an endotoxin concentration.

Further, as conventional endotoxin measurement methods, for example, ones described in Patent Literatures 1 to 5 have already been employed.

Patent Literature 1 is a method of stabilizing an endotoxin in an aqueous solution, the method including causing a water-soluble protein that has an affinity for the endotoxin and does not have such property as to inhibit or accelerate a reaction between the endotoxin and a horseshoe crab amebocyte lysate to coexist in the aqueous solution containing the endotoxin to accurately measure an endotoxin concentration in the aqueous solution over along time period.

Patent Literature 2 is a method including causing a peptide derivative (or protein) having such property as to bind to an endotoxin to suppress the activity of the endotoxin and a surfactant to coexist in a sample containing the endotoxin to suppress the activity of the endotoxin.

Patent Literature 3 is a method including mixing a horseshoe crab amebocyte lysate and a sample containing an endotoxin or a β-D-glucan in the coexistence of a predetermined water-soluble polymer, measuring a time period required for the degree of an optical change to reach a predetermined value, and determining the amount of the endotoxin or the like in the sample on the basis of a correlation between the obtained time period and the amount of the endotoxin or the like to detect the endotoxin or the like by means of a turbidimetric time assay with high sensitivity.

Patent Literature 4 is a measurement apparatus for measuring a target substance in a sample through a gelation reaction to accurately measure the concentration of a substance to be measured by the gelation reaction such as an endotoxin or a β-D-glucan within a short time period, the apparatus being a technology in which a sample cuvet storing a solution containing an analyte containing the substance to be measured and a reagent causing gelation is irradiated with illuminating light from a light-emitting diode, the solution in the sample cuvet is agitated with a stirrer bar to produce minute and uniform gel particles, and is then passed through the illuminating light, transmitted light from the gel particles produced in the sample cuvet is detected with a diode, and the concentration of the substance in the solution is measured on the basis of the transmitted light detection output.

Patent Literature 5 is a technology including a sample cuvet, a reagent that is stored in the sample cuvet in advance and reacts with a target substance in a sample to gelate, a stirring member that is stored in the sample cuvet in advance and stirs a mixing solution formed of the injected sample and reagent to suppress the gelation of the entirety of the agitated solution, and a sealing member which seals the opening of the sample cuvet in a state where the reagent and the stirring member are stored in the sample cuvet, and through which the sample can be injected into the sample cuvet after the sealing, in which a stirring operation by the stirring member is started at the time point at which the sample is injected into the sample cuvet and gel particles are produced in a state where the gelation of the entirety of the agitated solution is suppressed.

Further, the measurement technology using a gelation reaction is employed for measuring not only the endotoxin described above but also a β-D-glucan or the like.

The β-D-glucan is a polysaccharide constituting cell membranes specific to fungi. Measurement of the β-D-glucan is effective for screening a wide variety of fungi responsible for fungal infection, including not only fungi found in a general clinical environment, such as *Candida, Aspergillus*, or *Cryptococcus*, but also fungi rarely found in the general clinical environment.

The phenomenon that the gelation of the horseshoe crab amebocyte lysate is caused by the β-D-glucan is employed in the measurement of the β-D-glucan as well. The measurement is carried out by the above-mentioned gelation method, turbidimetric time assay, or synthetic chromogenic substrate method.

Measurement techniques for the endotoxin and the β-D-glucan have common points. For example, almost the same kind of measurement hardware is used to remove a Factor G component, which specifically reacts with the β-D-glucan, from the horseshoe crab amebocyte lysate, and hence a gelation reaction or chromogenic reaction selective for the endotoxin can be measured. Alternatively, the endotoxin in a sample is inactivated by pretreatment, and hence a gelation reaction or chromogenic reaction selective for the β-D-glucan can be measured.

[PTL 1] JP 2817606 B2 (Configuration of Invention)
[PTL 2] JP 3106839 B2 (Configuration of Invention)
[PTL 3] JP 3327076 B2 (Configuration of Invention)
[PTL 4] WO 2008-139544 A1 (Embodiment of Invention and FIG. 1)
[PTL 5] JP 2010-085276 A (Best Mode for carrying out Invention and FIG. 1)

SUMMARY OF INVENTION

Technical Problem

However, the conventional gelation method, turbidimetric time assay, and synthetic chromogenic substrate method have the following drawbacks.

Both the gelation method and the turbidimetric time assay need as long a time period as about 90 minutes or more at a low concentration for the production of gels to take place. That is, although the gelation time of a reaction solution is proportional to the concentration of a target substance in a sample as a measuring object, it is not possible to detect the accurate gelation initiation time or the like by both the gelation method and the turbidimetric time assay because of inferior sensitivity, and hence a reaction amount is calculated based on a time period required for the gelation to progress to some extent, and is used as a guideline for the gelation time.

The turbidimetric time assay is taken as an example. The turbidimetric time assay shows a turbidity at the initial concentration level at which a change starts and a turbidity at the concentration level at which the change reaches a saturation point because reagents are prepared under the same conditions. However, the time point at which the change of the turbidity of each reagent, which changes like a sigmoid curve, starts and the time point at which the change ends are difficult to understand, and hence the assay is estimated as a quantitative method by measuring the arrival of the change (increase in turbidity) at a certain level between the initial and final levels instead of observing the change during the entire gelation. However, when the concentration of the endotoxin is low, the gelation of the entire system is delayed, and at the same time, a change in turbidity to be observed is delayed, resulting in a difficulty in measuring the arrival of the change at a certain level. As a result, sensitivity inevitably lowers.

Thus, it is hard to say that both the gelation method and the turbidimetric time assay are suitable for the case where emergency is required and for the measurement of many specimens. Further, when the turbidimetric time assay is carried out, non-specific turbidity irrelevant to the endotoxin occurs in some cases, and hence the turbidimetric time assay may lack measurement accuracy. In addition, the critical concentration for measurement in the gelation method is 3 pg/ml, and the critical concentration for measurement in the turbidimetric time assay is about 1 pg/ml.

It should be noted that even when the scattering photometry disclosed in Patent Literature 1 or the like is applied as the turbidimetric time assay applied to a gelation reaction measurement apparatus, the scattering photometry is a quantification method in which the observation of the change of the gelation of the entire solution is not carried out, and hence the above-mentioned problems under agitating condition cannot be solved.

On the other hand, the measurement time of the synthetic chromogenic substrate method is as short as about 30 minutes compared with those of the gelation method and the turbidimetric time assay. However, in the measurement of a natural substance such as a clinical sample, a false-positive reaction due to the coexistent non-specific protease occurs as a negative effort of the use of an artificial substrate in some cases. Particularly in the clinical sample or the like, it is difficult to carry out the measurement with high specificity, which causes such a problem that the reliability of the measurement is lost. In addition, preparation for measurement is troublesome, and the critical concentration for measurement is 3 pg/ml, which is inferior to the turbidimetric time assay.

In addition, each of Patent Literatures 1 and 2 is predicated on long-term measurement for the endotoxin, and merely provides a method of stabilizing the endotoxin in the aqueous solution or suppressing the activation of the endotoxin.

In addition, Patent Literatures 3 and 4 are each predicated on the turbidimetric time assay. Accordingly, in order that the amount of the endotoxin may be determined, the following is needed. The gelation of the entire solution is caused, the rate of the gelation is measured in terms of turbidity under settled condition, and the concentration of the endotoxin is calculated.

In this respect, Patent Literature 5 is a system previously applied by the applicant of the present application and the following attempt has been made in the literature. A sample containing, for example, the endotoxin is mixed with a reagent, gel particles are caused to appear while the gelation of the entirety of the agitating solution is suppressed, and the timing of the appearance of the gel particles is detected with optical detection device.

While an object to be detected by, for example, each of the systems of Patent Literatures 3 and 4 is the gelled state of the entirety of the agitating solution, an object to be detected by the system is the time point of the initiation of the production of the gel particles corresponding to the time point at which the agitating solution undergoes a phase transition from a sol phase to a gel phase. Accordingly, the system is superior to the systems of Patent Literatures 3 and 4 in that the phenomenon of the transition of the mixing solution to a gel can be grasped within a short time period with high sensitivity.

The applicant of the present application has found a novel gel particle measurement reagent that controls a stable phase transition of the agitating solution from a sol phase to a gel phase for enabling additionally comfortable employment of such system, and have finally come up with the present invention.

The present invention provides a gel particle measurement reagent effective in quickly measuring the time point of the initiation of the production of gel particles and a measurement method using the reagent.

Solution to Problem

First aspect of the invention according to claim 1 is a gel particle measurement reagent to be used to be agitated continuously with a sample containing a target substance as a measuring object to turn the target substance into gel particles, including: a reagent base material that undergoes a gelation reaction with the target substance; and a biologically inactive particle formation accelerating factor that is added to the reagent base material, has solubility in the sample and dissolves therein at a concentration of 0.002 to 1%, and accelerates the production of gel particles whose particle sizes are centered in a predetermined range.

Second aspect of the invention according to claim 2 is a gel particle measurement reagent according to claim 1, in which the particle formation accelerating factor includes a soluble, thermally denatured protein.

Third aspect of the invention according to claim 3 is a gel particle measurement reagent according to claim 1, in which the particle formation accelerating factor is a soluble, inactive, biogenic polymer or a petroleum polymer chemical component-derived porous fine particle.

Forth aspect of the invention according to claim 4 is a gel particle measurement apparatus according to any one of claims 1 to 3, in which: the target substance as the measuring object is an endotoxin or a β-D-glucan; and the reagent base material includes a limulus reagent.

Fifth aspect of the invention according to claim 5 is a gel particle measurement method of measuring a target substance in a sample turned into particles by a gelation reaction under agitated condition, the method including: a storing step of storing, in a sample cuvet at least partially having an incident portion through which light enters and an exit portion through which the light exits, a sample containing the target substance as a measuring object and a solution containing the gel particle measurement reagent according to any one of claims 1 to 4 causing the gelation of the target substance; a stirring step of stirring a mixing solution formed of the sample and the solution of the reagent in the sample cuvet with stirring device to suppress gelation of the entirety of the mixing solution; a light irradiation step of irradiating the agitating solution formed of the sample and the solution of the reagent in the sample cuvet with coherent light from an incident light source provided outside the incident portion of the sample cuvet; a detecting step of detecting a light component scattered from or transmitted through gel particles to be produced in the agitating solution formed of the sample and the solution of the reagent in the sample cuvet at a time point at which the agitating solution undergoes a phase transition from a sol phase to a gel phase with detection device provided outside the exit portion of the sample cuvet; and a gel particle production determining step of determining a time point of the initiation of the production of the gel particles in the agitating solution based on a detection output obtained in the detecting step.

Advantageous Effects of Invention

According to first aspect of the invention according to claim 1, the gel particle measurement reagent effective in quickly measuring the time point of the initiation of the production of gel particles can be provided.

According to second or third aspect of the invention according to claim 2 or 3, the gel particle measurement reagent can be easily produced with a representative particle formation accelerating factor.

According to forth aspect of the invention according to claim 4, the reagent can be applied to the quantitative determination of the endotoxin or β-D-glucan as a target substance to be measured.

According to fifth aspect of the invention according to claim 5, the time point of the initiation of the production of the gel particles can be quickly measured under agitated condition.

DESCRIPTION OF EMBODIMENTS

Summary of Embodiments

Figure 1A:
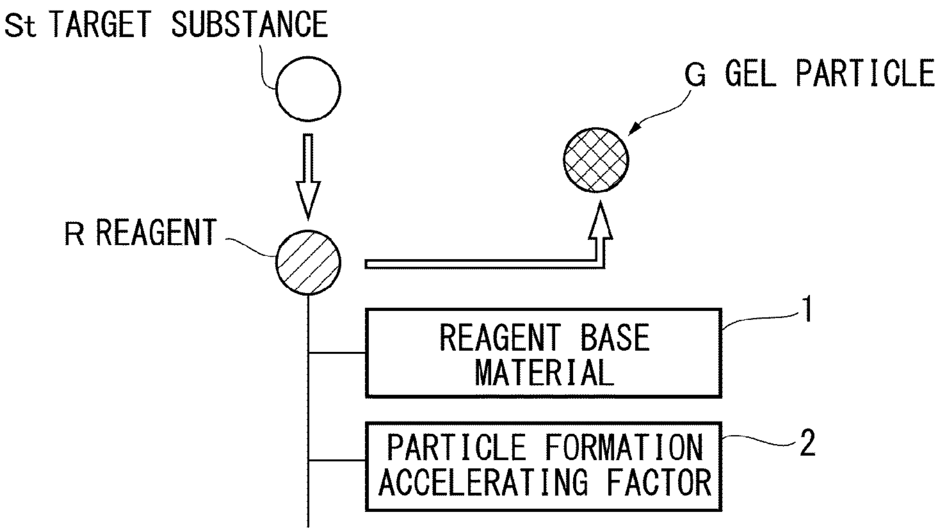
FIG. 1A is an explanatory diagram illustrating the outline of an embodiment of a gel particle measurement reagent to which the present invention is applied.

FIG. 1A is an explanatory diagram schematically illustrating a gel particle measurement reagent according to embodiments to which the present invention is applied.

In the figure, a gel particle measurement reagent R is used to be agitated continuously with a sample S (see FIG. 1B) containing a target substance St as a measuring object to turn the target substance St into gel particles, and contains a reagent base material 1 that undergoes a gelation reaction with the target substance St and a biologically inactive particle formation accelerating factor 2 that is added to the reagent base material 1, has solubility in the sample S and dissolves therein at a concentration of 0.002 to 1%, and accelerates the production of gel particles G whose particle sizes are centered in a predetermined range. It should be noted that the concentration value of the particle formation accelerating factor 2 in the present application is represented in the unit of a volume percent (v/v).

In the figure, the presence of the reagent R that specifically reacts with the target substance St of the sample S causes a phenomenon in which the target substance St specifically reacts with the reagent R at a ratio dependent on the concentration of the target substance St in the sample S. In the reaction process, the following occurs. The reagent R receives a stimulus from the target substance St to activate a predetermined factor and, for example, in agitated condition, a water-soluble protein is transformed into an insoluble protein at the timing at which a predetermined enzyme is activated as a result of the activation through a decomposition reaction by the enzyme, thereby leading to the appearance of the gel particles G.

In this embodiment, a wide variety of substances are included in the category of the target substance St as long as the substances each undergo a gelation reaction with the measurement reagent R to produce the gel particles G. Examples of the substance include an endotoxin and a β-D-glucan.

In addition, the reagent base material 1 has only to contain a factor (such as an enzyme) that undergoes a gelation reaction with the target substance St. For example, when the target substance St is the endotoxin or the β-D-glucan, the reagent base material is representatively a limulus reagent but is not limited to the limulus reagent. Of course, when factors in the horseshoe crab amebocyte lysate except a limulus amebocyte lysate each specifically react with the endotoxin or the β-D-glucan, the reagent base material St may be produced by utilizing the amebocyte lysate.

Further, in agitated condition, the particle formation accelerating factor 2 needs to be soluble in the sample S. This is because if the factor is insoluble, the factor may serve as an obstruction in accurate grasping of the time point of the initiation of the production of the gel particles.

In addition, in agitated condition, the particle formation accelerating factor 2 has only to exert the following action. The factor serves as an aggregation factor for accelerating the aggregation of products leading to the gel particles G (such as a product of an enzyme) to accelerate the formation of the gel particles G. In this case, the particle formation accelerating factor 2 is assumed to exert an action of integrating coagulins as the final products of a limulus reaction leading to the formation of the gel particles G into a certain size.

Figure 2A:
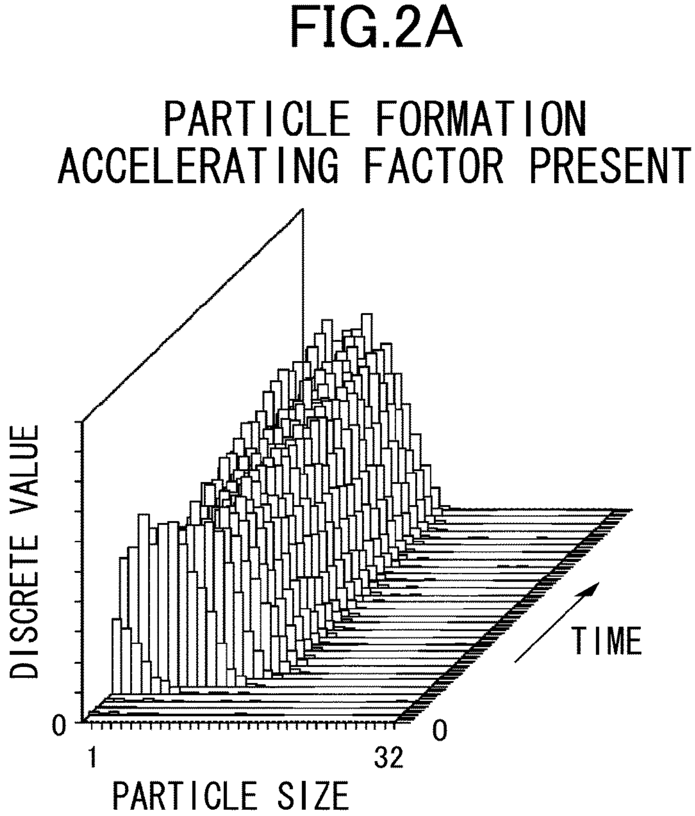
FIG. 2A is an explanatory diagram schematically showing the production process of gel particles to be produced upon use of the gel particle measurement reagent according to this embodiment and FIG. 2B is an explanatory diagram schematically showing the production process of gel particles to be produced upon use of a gel particle measurement reagent according to a comparative embodiment.

Here, the addition of the particle formation accelerating factor 2 does not produce various unlimited, amorphous particle sizes in association with the lapse of time as schematically shown in FIG. 2A but produces the products leading to the gel particles G whose particle sizes are centered in a predetermined range (range biased to a small S size with respect to particle size levels 1 to 32 in FIG. 2). The aggregation of the products quickly leads to the gel particles G. With regard to the phrase “particle sizes in a predetermined range” as used herein, the particles have only to be of such relatively small sizes as to aggregate easily and their particle sizes have only to fall within a certain range.

Figure 2B:
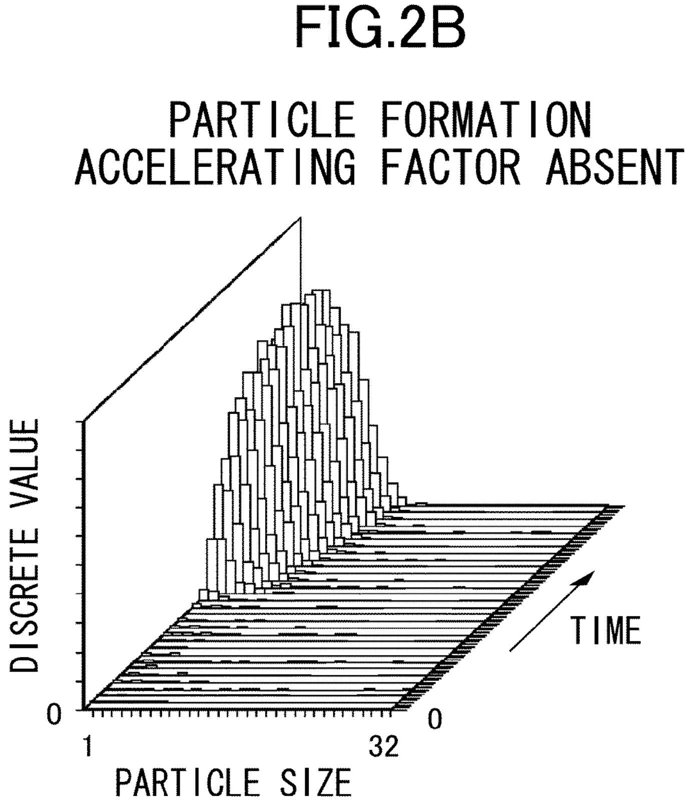

It should be noted that for reference, it is understood that in the production process of the gel particles G in the agitated gelation reaction in the case where the particle formation accelerating factor 2 is not added, as schematically shown in FIG. 2B, the products leading to the gel particles G are produced in a state where the particle sizes are not centered in a predetermined range, and the timing of the production of the products is slow as compared with that in the case where the particle formation accelerating factor 2 is added.

In addition, the concentration of the particle formation accelerating factor 2 needs to be 0.002 to 1%. In this case, a concentration of less than 0.002% is insufficient to accelerate the formation of the gel particles G, and on the other hand, a concentration in excess of 1% shows such a tendency that an excessive amount of the particle formation accelerating factor 2 is added to suppress the aggregation reaction conversely. This is assumed to be because an excessively large amount of the particle formation accelerating factor 2 results in the dispersion of coagulin molecules, thereby leading to such a result that the molecules interfere with each other instead of interacting with each other under agitating condition.

Further, the particle formation accelerating factor 2 needs to be biologically inactive. This is because of the following reason. In the case of, for example, a biologically active factor, the characteristics of the factor change in association with its activity, and hence the action of the factor becomes instable and the factor may affect the reaction itself by the reagent base material 1.

Here, a representative embodiment of the particle formation accelerating factor 2 is, for example, a soluble, thermally denatured protein. Examples of the thermally denatured protein include plasma proteins, enzymes, plant proteins, and ovalbumin. For example, a plasma protein is obtained as a soluble, thermally denatured protein by subjecting its dilute solution to a heat treatment (e.g., a high-pressure sterilization treatment at 120° C. for 20 minutes).

In addition, the particle formation accelerating factor 2 is not necessarily needed to be a thermally denatured protein because the factor has only to be a substance serving as a core for minute gelation, i.e., particle formation. Another representative embodiment of the particle formation accelerating factor 2 is a biogenic polymer or a petroleum polymer chemical component-derived porous fine particle, provided that each of the polymer and the fine particle also needs to be soluble and biologically inactive.

Examples of the biogenic polymer include celluloses, polysaccharides, and glycoproteins. In addition, examples of the petroleum polymer chemical component-derived porous fine particle include nanoparticle resins.

Next, the outline of a gel particle measurement method using the gel particle measurement reagent R in this embodiment is described.

Figure 1B:
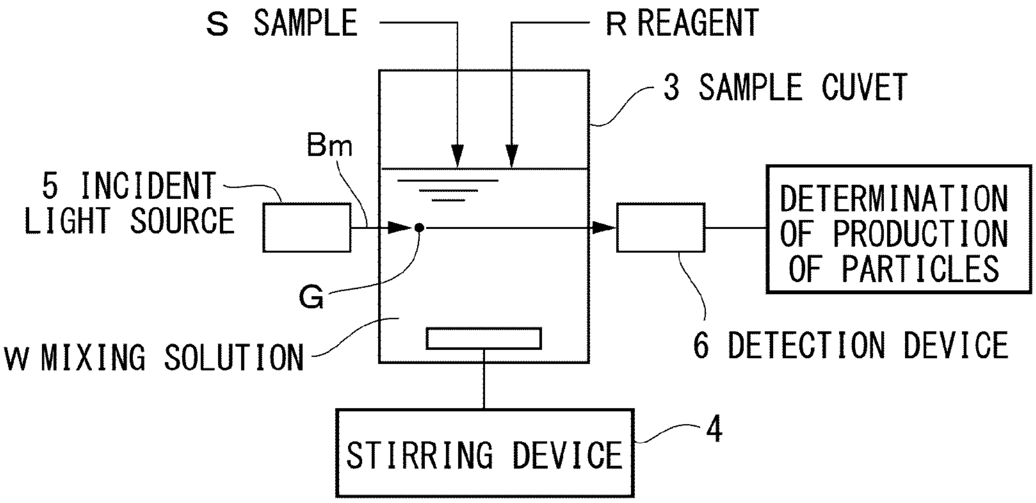
FIG. 1B is a schematic view illustrating a gel particle measurement method to be adopted in this embodiment.

As illustrated in FIG. 1B, in this embodiment, a gel particle measurement method is a gel particle measurement method of measuring a target substance St in a sample S turned into particles by a gelation reaction, the method including: a storing step of storing, in a sample cuvet 3 having an incident portion on at least part of which light is incident and an exit portion from which the light is caused to exit, a sample S containing the target substance St as a measuring object and a solution containing the gel particle measurement reagent R causing gelation of the target substance St; a stirring step of stirring a mixing solution W formed of the sample S and the solution of the reagent R in the sample cuvet 3 with stirring device 4 to suppress gelation of an entirety of the mixing solution; a light irradiation step of irradiating the mixing solution W formed of the sample S and the solution of the reagent R in the sample cuvet 3 with coherent light from an incident light source 5 provided outside the incident portion of the sample cuvet 3; a detecting step of detecting a light component scattered from or transmitted through gel particles G to be produced in the mixing solution W formed of the sample S and the solution of the reagent R in the sample cuvet 3 at a time point at which the mixing solution W undergoes a phase transition from a sol phase to a gel phase with detection device 6 provided outside the exit portion of the sample cuvet 3; and a gel particle production determining step of determining a time point of initiation of the production of the gel particles G in the mixing solution W based on a detection output obtained in the detecting step.

In such gel particle measurement method, the sample cuvet 3, the stirring device 4, the incident light source 5, the detection device 6, and a control apparatus (not shown) (such as a computer) are used.

Here, the sample cuvet 3 has only to have the incident portion on at least part of which light is incident and the exit portion from which the light is caused to exit, and its shape is not limited to one having a cylindrical peripheral wall and may be one having a polygonal peripheral wall. Further, from the viewpoint of keeping a measurement condition of a limulus reaction as an enzyme reaction constant, a preferred embodiment is that the sample cuvet 3 is provided in a thermostatic chamber (not shown).

Further, the stirring device 4 includes a wide range of means as long as the means provides a stirring action to the mixing solution W formed of the sample S and the solution of the reagent R. An embodiment in which the means is built in and directly performs stirring may be included of course, and any embodiment may be suitably selected from, for example, an embodiment in which a stirring action is provided by air and an embodiment in which a stirring action is provided by shaking.

In addition, the degree of stirring by the stirring device 4 is required to be such that the entire mixing solution W formed of the sample S and the solution of the reagent R in the sample cuvet 3 is inhibited from gelating.

In particular, from the viewpoint that stirring movement by the stirring device 4 may be conducted for sure, it is preferred that the sample cuvet 3 include, in a cell container, the stirring device 4 which is capable of directly stirring the mixing solution W formed of the sample S and the solution of the reagent R during measurement of gel particle formation.

In addition, the incident light source 5 is not limited to the laser light source for emitting laser light as long as coherent light is emitted. For example, the incident light source 5 may also be constructed by passing monochromatic light such as light of a sodium lamp through a pin hole, and may have a configuration using a high-brightness LED and a filter.

In addition, the detection device 6 may be provided at a site different from that of the incident light source 5 to detect scattered light or transmitted light, or may be provided on the same side as that of the incident light source 5 to detect a scattered light component returning to the rear of the incident light source.

For example, in an embodiment in which the detection device 6 is provided at a site different from that of the incident light source 5, the means may detect any one of the transmitted light and the scattered light. However, in, for example, the case where a transmitted light detection system is adopted in such an embodiment that the transmitted light and the scattered light are simultaneously present at the site where the detection device 6 is provided, the following embodiment is preferred. Scattered light-removing means for removing a component traveling toward the detection device 6 out of the scattered light scattered by the gel particles G and subjected to a phase shift is provided between the detection device 6 and the sample cuvet 3. The scattered light-removing means is, for example, a deflection filter that cuts off a scattered light component and transmits only a transmitted light component. It should be noted that in contrast, an embodiment in which the transmitted light is removed by transmitted light-removing means on the basis of the same principle is preferred for a system involving detecting the scattered light.

On the other hand, for example, when the detection device 6 detects backscattered light, an embodiment in which the backscattered light component is directly detected around the incident light from the incident light source 5 is permitted, and an embodiment in which light beams around the incident light from the incident light source 5 are collected and then guided with a light-guiding member such as a glass fiber to an arbitrary place to be detected is also permitted. In addition, stray light-removing means (such a structure that a light-absorbing material is provided in the peripheral wall of the sample cuvet 3 or outside the sample cuvet, or light is irregularly reflected in the sample cuvet) for removing a stray light component is preferably adopted to prevent a transmitted light or scattered light component that does not return to the side of the incident light source 5 in the mixing solution W out of the light incident from the incident light source 5 from being detected as stray light by the detection device 6 for the backscattered light.

Further, a computing apparatus has only to embody the gel particle production determining step and the following approach has been representatively adopted. The variation component of the detection output is measured on the basis of the result of the detection of the detection device 6 and then the time point of the initiation of the production of the gel particles G in the mixing solution W is determined on the basis of the result of the measurement.

Here, the approach for measuring the variation component of the detection light is, for example, an approach that applies filtering to the detection output while applying averaging or smoothing thereto.

In addition, the computing apparatus is an apparatus that determines the time point of the initiation of the production of the gel particles G but is not limited to such apparatus, and may widely determine the production state of the gel particles G. The phrase "determine the production state of the gel particles" as used herein of course includes direct determination of information regarding the production state of the gel particles, and also includes determination of information that can be determined based on the production state of the gel particles (for example, quantified information on a target substance). Here, the phrase "the production state of the gel particles G" widely includes the time point of the production start (appearance) of the gel particles, a change in the production process of the gel particles, the time point of the production finish of the gel particles, and the production amount of the gel particles. Thus, in this embodiment, the phrase may include other matters, as long as the phrase includes at least the timing of the phase transition of the mixing solution W from a sol phase to a gel phase.

Figure 1C:
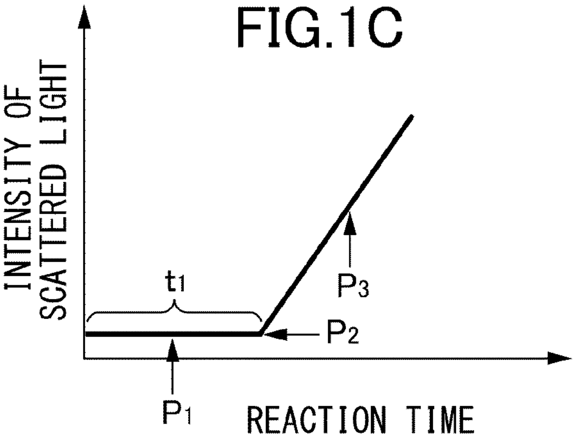
FIG. 1C is an explanatory diagram showing a relationship between a reaction time and the intensity of scattered light in the progressing step of a gelation reaction as a measurement principle by the measurement method of FIG. 1B.

Next, the principle of the measurement of the time point of the initiation of the production of the gel particles G by the gel particle measurement method illustrated in FIG. 1B (adopting, for example, the scattered light detection system) is described with reference to FIG. 1C.

In this embodiment, in the case where the mixing solution W of the sample S and the solution of the reagent R is free of the gel particles G unlike the illustration of FIG. 1B (corresponding to the case where the mixing solution W is in a sol phase), irradiation light Bm from the incident light source 5 is not blocked by any gel particle. Accordingly, the irradiation light Bm is not scattered by the gel particles B and hence no scattered light component to be detected by the detection device 6 exists. Accordingly, the intensity of the scattered light to be detected by the detection device 6 is kept at substantially 0 (see $P_1$ of FIG. 1C).

Then, in the case where the gel particles G start to be produced in the mixing solution W of the sample S and the solution of the reagent R as illustrated in FIG. 1B (corresponding to the case where the mixing solution W starts to undergo a phase transition from the sol phase to a gel phase), the irradiation light Bm from the incident light source 5 is partially blocked by the presence of the gel particles G. Accordingly, the irradiation light Bm is scattered and the scattered light component is detected by the detection device 6. Accordingly, the detection output by the detection device 6 tries to rise and change from a 0 level as a stable region (see $P_2$ of FIG. 1C).

After that, in the case where the production of the gel particles G in the mixing solution W of the sample S and the solution of the reagent R gradually progresses as illustrated in FIG. 1B, the degree to which the irradiation light Bm from the incident light source 5 is scattered gradually increases by virtue of the presence of a large number of the gel particles G to be sequentially produced, and the quantity of the scattered light component to be detected by the detection device 6 also gradually increases. Accordingly, the detection output by the detection device 6 sequentially increases and hence the intensity of the scattered light to be detected by the detection device 6 sequentially rises and changes from a change point $P_2$ as a border (see $P_3$ of FIG. 1C).

Described in the foregoing embodiment is an embodiment in which the time point of the initiation of the production of the gel particles (corresponding to $P_2$ of FIG. 1C) leading to the timing at which the mixing solution W undergoes a phase transition from the sol phase to the gel phase is determined on the basis of the variation component of the scattered light of the irradiation light Bm with which the inside of the mixing solution W is irradiated.

Figure 3:
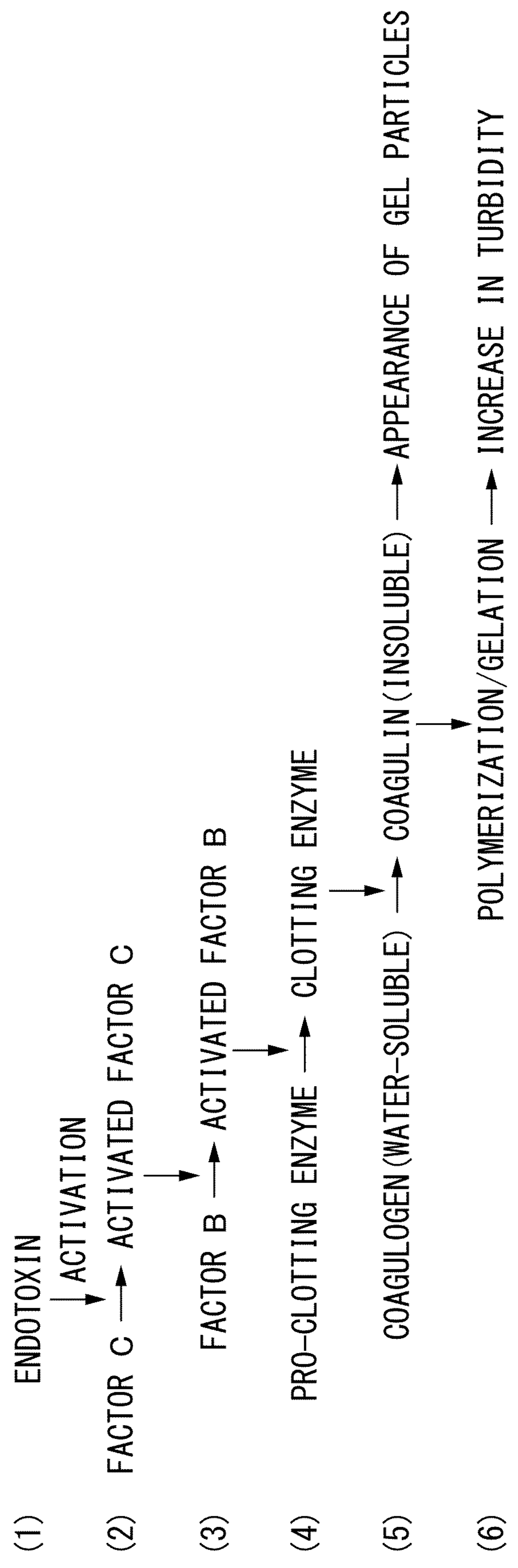
FIG. 3 is an explanatory diagram schematically illustrating the gelation reaction process of an endotoxin when a limulus reagent is used.

Next, by taking an endotoxin as an example, a process of the gelation reaction of the endotoxin is schematically illustrated in FIG. 3.

In the figure, after the stimulation of the endotoxin shown in (1) is delivered to a limulus reagent, Factor C is first activated into Activated Factor C as shown in (2). Next, the action of Activated Factor C causes the activation of Factor B, producing Activated Factor B as shown in (3). After that, the action of Activated Factor B causes the conversion of a proclotting enzyme to a clotting enzyme as shown in (4). As shown in (5), this clotting enzyme decomposes coagulogen (water-soluble protein), producing coagulin (insoluble protein). When stirring is performed under this condition, gelation of the entire coagulin (insoluble protein) is inhibited, and therefore a gel particle G of coagulin appears. On the other hand, when the coagulin is left to stand still, polymerization and gelation take place to the entire solution system as shown in (6).

That is, in the case where the target substance St in the sample S is an endotoxin, when the stimulation of the endotoxin is delivered to the limulus reagent R while providing a constant agitating state to a mixing solution W to inhibit the gelation of the entire mixing solution W, the limulus reagent R can cause the production of the gel particles G of coagulin (insoluble protein) around the clotting enzyme. Thus, it is understood that after a gel particle G of coagulin (insoluble protein) is produced, a reaction process in which the gel particles G are subsequently produced follows.

In addition, it was found that a rate at which the stimulation of the endotoxin was delivered to a flow of a reaction (cascade) of the limulus reagent R (limulus reaction rate) was dependent on an endotoxin concentration, and that as the endotoxin concentration was higher, the limulus reaction rate was higher, and the timing of the appearance of the gel particles G formed of coagulin (insoluble protein) was earlier.

Thus, if changes in scattered light or transmitted light are detected in a mixing solution with high accuracy, the timing of the appearance of the gel particles G formed of coagulin (insoluble protein) can be observed as the time point of the initiation of the production of the gel particles G. This is a fundamental of the gel particle measurement method according to this embodiment.

The measuring principle of the gel particle measurement method described above is completely different from, for example, the measuring principle of the conventional gelation method or conventional turbidimetric time assay (an embodiment in which in the reaction process by the limulus reagent R under settled condition, the gelation of the entire solution in the reaction system finally occurs owing to the influence of an activated clotting enzyme, and a process in which the entire system homogeneously gelates is quantitatively measured based on the turbidity).

In general, in the first place, measurement of an endotoxin in a clinical sample is required to be performed easily and quickly, in particular, for the purpose of emergency medical care.

Problems of "insufficient measurement caused by poor sensitivity" and "inconvenience caused by long measurement time" in a conventional turbidimetric time assay can be solved with more reliability by the above-mentioned measurement method.

That is, in principle, the gel particle measurement method according to this embodiment is configured as described below. That is, the mixing solution W formed of a sample and a limulus reagent is continuously agitated homogeneously to produce minute gel particles locally, not in the entire mixing solution system, under the homogeneous reaction. The gel particles are irradiated with coherent uniform light such as laser light to cause scattering of light. The scattered light is detected so as to detect a phase transition point leading to a phase transition from a sol phase to a gel phase, which is appearance of gel particles due to the addition of an endotoxin. A time that elapses before the phase transition point is measured. In this manner, the amount of an endotoxin in the limulus reagent can be estimated.

In summary, the gel particle measurement method according to this embodiment is configured without keeping track of a change (gelation) in the entire mixing solution system, paying attention to the fact that the timing of the phase transition (time point of the initiation of the production of gel particles) depends on an endotoxin concentration. Thus, an endotoxin can be detected more quickly and obviously compared with the conventional turbidimetric time assay.

The present invention is hereinafter described in more detail based on embodiments illustrated in the attached drawings.

First Embodiment

A gel particle measurement apparatus according to a first embodiment of the present invention includes a sample cuvet 100 into which a sample containing an endotoxin is injected, and measures the endotoxin concentration as a target substance in the sample, for example, through a gelation reaction using a limulus reagent.

—Gel Particle Measurement Apparatus—

Figure 4:
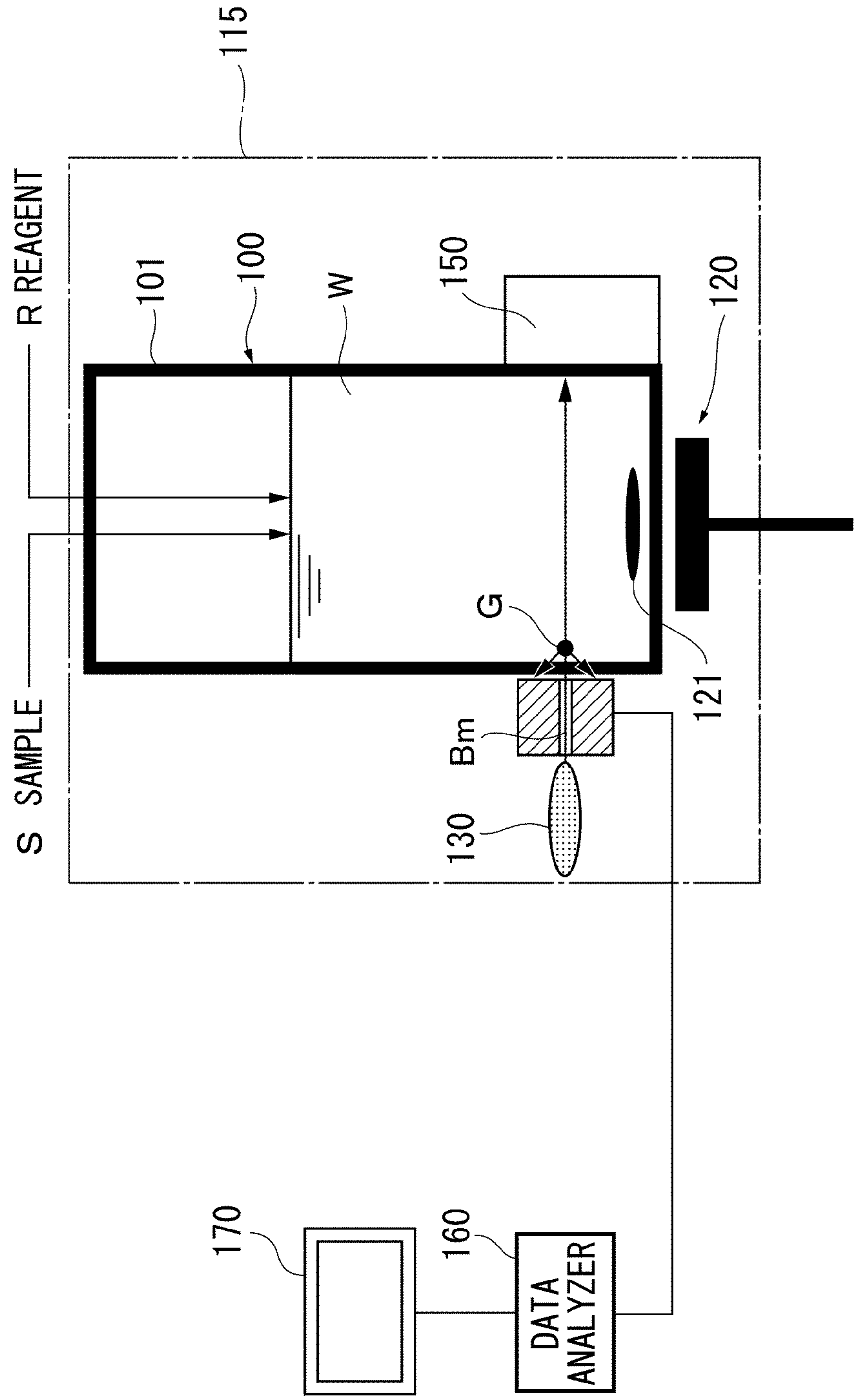
FIG. 4 is an explanatory diagram illustrating a gel particle measurement apparatus according to a first embodiment of the present invention.

In this embodiment, the gel particle measurement apparatus is configured as illustrated in FIG. 4.

In the figure, the sample cuvet 100 is set on a predetermined measurement stage, and in this embodiment, the sample cuvet 100 is placed in a thermostatic chamber 115 so that the mixing solution W formed of the sample S and the reagent R is placed under a constant thermostatic environment (for example, 37° C.), thereby keeping a measuring condition constant.

In this embodiment, the sample S containing an endotoxin as a target substance is a subject.

Meanwhile, the reagent R contains a limulus reagent that undergoes a gelation reaction with the endotoxin as a reagent base material and a particle formation accelerating factor added to the limulus reagent. Here, a thermally denatured protein (such as a plasma protein or ovalbumin) soluble in the sample S is used as the particle formation accelerating factor and the factor is adjusted so that its concentration may be 0.002 to 1% with respect to the sample S.

Here, the particle formation accelerating factor may be provided together with the limulus reagent, or may be provided separately from the limulus reagent. A representative embodiment of the former is an embodiment in which a product obtained by adding the particle formation accelerating factor to the limulus reagent in advance is constituted so as to be of, for example, a freeze-dried powder shape. In addition, a representative embodiment of the latter is the following embodiment. The sample R such as blood for measurement is diluted and hence a diluent containing the particle formation accelerating factor is provided separately from the limulus reagent of, for example, a freeze-dried powder shape. It should be noted that in the latter embodiment, the diluent needs to be sufficiently stirred together with the limulus reagent before the gelation reaction so that the particle formation accelerating factor may coexist with the limulus reagent at the time of the gelation reaction.

In addition, reference symbol 120 represents a stirring-driving device for driving a magnetic stirrer bar 121 in the sample cuvet 100 so as to stir the mixing solution W in the sample cuvet 100, and the stirring-driving device 120 is structured so that, for example, a constant stirring state is provided to the mixing solution W, to thereby inhibit the entire mixing solution W from being gelating while stirring the mixing solution W homogeneously.

In particular, in this example, the stirring-driving device 120 is configured as a stirring-driving source (magnetic stirrer) to apply its stirring force due to a magnetic force to the stirrer bar 121 which is formed of a magnetic material and built in the bottom wall of the sample cuvet 100.

In addition, reference symbol 130 represents a laser light source which is installed outside the side peripheral wall of the sample cuvet 100 and emits coherent light.

Figure 5A:
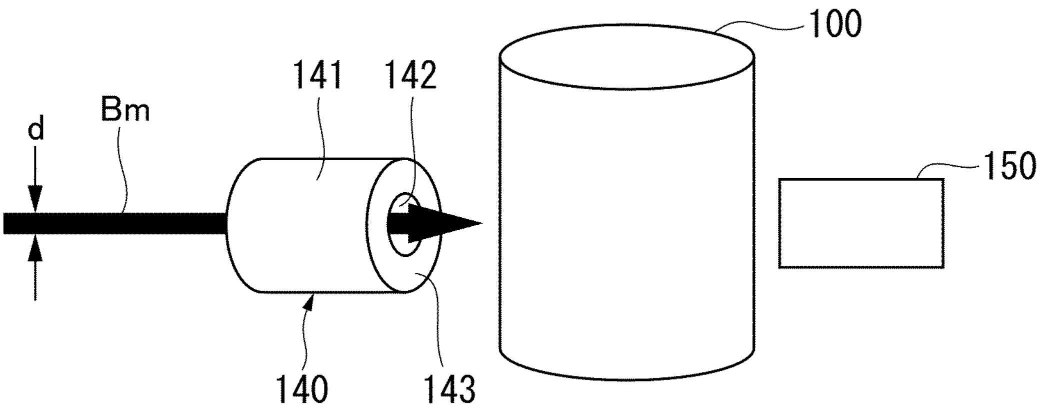
FIG. 5A is an explanatory diagram illustrating a configuration example of a laser light source and a backscattered light detector used in the first embodiment and FIG. 5B is an explanatory partial cross-sectional plan view of FIG. 5A.
Figure 5B:
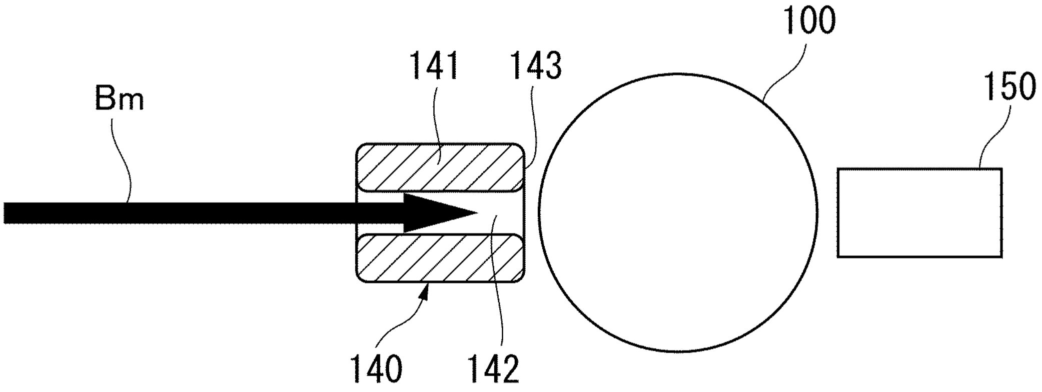

In this example, coherent light Bm from the laser light source 130 is, as illustrated in FIGS. 5A and 5B, emitted along a route that runs across the near-diameter line of the sample cuvet 100, and a diameter d of the light is set to a value (for example, about 5 to 20 μm) sufficiently larger than the diameter (for example, about 0.2 to 2 μm) of each of the produced gel particles.

Further, reference symbol 140 represents a backscattered light detector provided outside the sample cuvet 100 on the same side on which the laser light source 130 is provided, the backscattered light detector 140 detecting a backscattered light component, which returns to the side of the laser light source 130, out of the irradiation light Bm from the laser light source 130 scattered by the gel particles produced in the mixing solution in the sample cuvet 100.

In this example, the backscattered light detector 140 includes a cylindrical detector body 141 in which a passage hole 142 is opened at the center. The passage hole 142 of the detector body 141 allows irradiation light emitted from the laser light source 130 into the sample cuvet 100 to pass therethrough. A ring-shaped detecting surface 143 is provided on the detector body 141 so as to be opposed to a side peripheral wall outer surface of the sample cuvet 100, and further, a light-receiving element (not shown) such as a photodiode capable of sensing scattered light detected by the ring-shaped detecting surface 143 is incorporated into a part of the detector body 141.

In this case, the detection accuracy of the backscattered light detector 140 is set to such a degree as to detect a change in backscattered light quantity caused by the presence or absence of one to several gel particles in a passage area of the irradiation light Bm from the laser light source 130.

Although the ring-shaped detecting surface 143 of the backscattered light detector 140 may be placed in contact or in no contact with the side peripheral wall outer surface of the sample cuvet 100, it is preferred to place the ring-shaped detecting surface 143 in contact with the side peripheral wall outer surface from the viewpoint of keeping a satisfactory detection performance of a backscattered light component.

Further, in this embodiment, a stray light-removing member 150 is provided outside the sample cuvet 100 and on an opposite side of the laser light source 130 with respect to the sample cuvet 100.

The stray light-removing member 150 is configured so that a light absorbing member is provided correspondingly to a region of the sample cuvet 100 in which the irradiation light Bm emitted from the laser light source 130 into the sample cuvet 100 to pass through the sample cuvet 100 directly reaches a peripheral wall on the opposite side of the sample cuvet 100, and a peripheral region thereof.

The reason for providing the stray light-removing member 150 in a part of the sample cuvet 100 as described above is as follows. That is, a scattered light component except a backscattered light component returning to the side of the laser light source 130 out of the irradiation light from the laser light source 130 scattered, for example, by gel particles, or a transmitted light component directly passing through the periphery of the produced gel particles can be stray light components reflected from the inner wall of the sample cuvet 100 and directed to the backscattered light detector 140. Of those, in particular, a stray light component having high directivity is a transmitted light component and a scattered light component directed in the same direction as that of the transmitted light component, and hence, the stray light-removing member 150 is provided at a position corresponding to these light components.

Figure 8:
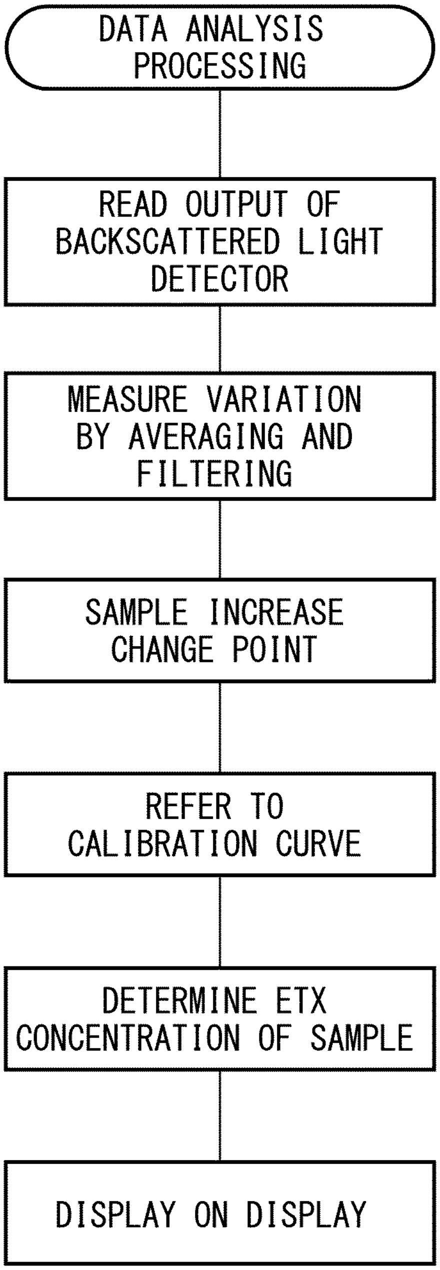
FIG. 8 is a flow chart illustrating an example of a data analysis processing of the gel particle measurement apparatus according to the first embodiment.

Reference symbol 160 represents a data analyzer which captures a detection output from the backscattered light detector 140 and carries out such data analysis processing as illustrated in FIG. 8, for example. Reference symbol 170 represents a display for displaying the results of the analysis performed with the data analyzer 160.

The data analyzer 160 is configured of a computer system including a CPU, a ROM, a RAM, an I/O interface, and the like. For example, a data analysis processing program illustrated in FIG. 8 is preliminarily installed in the ROM, and the data analysis processing program is executed with the CPU based on the detection output from the backscattered light detector 140.

It should be noted that the detection output from the backscattered light detector 140 is, for example, subjected to current-voltage conversion in an amplifier (not shown) before subjected to AD conversion in an AD converter, and is captured in the data analyzer 160.

<Configuration Example of Sample Cuvet>

Next, a configuration example of the sample cuvet 100 used in this embodiment and an example of introducing a stirrer bar 121 and a sample S into the sample cuvet 100 are described in detail with reference to FIGS. 6A and 6B.

In the figures, the sample cuvet 100 is formed of, for example, a bottomed cylindrical container 101 that is integrally molded with a glass material and has a circular shape in a lateral cross-section with an upper part opened. In an upper part of the cylindrical container 101, a flange portion 102 is formed, and a constricted portion 103 is formed below the flange portion 102. A small diameter hole portion 104 is formed at the flange portion 102 and the constricted portion 103, and a large diameter space portion 105 larger in diameter than the small diameter hole portion 104 is formed inside the cylindrical container 101.

Then, in the sample cuvet 100, a reagent 106 causing a gelation reaction with a sample containing an endotoxin is stored, for example, in a freeze-dried powder shape in advance sterilely without an endotoxin (generally referred to as "endotoxin-free" or "pyrogen-free"), and the stirrer bar 121 using a magnetic material is stored in advance.

Further, a sealing stopper 108 made of an elastic material such as rubber is fitted in the small diameter hole portion 104 of the sample cuvet 100. The sealing stopper 108 is formed into a substantially T-shape in cross-section. A head portion 108*a* of the sealing stopper 108 is placed on the flange portion 102 of the sample cuvet 100, and a leg portion 108*b* of the sealing stopper 108 is inserted in the small diameter hole portion 104 in close contact therewith. It should be noted that a part of the leg portion 108*b* of the sealing stopper 108 is provided with a cutout 108*c*.

Further, the flange portion 102 of the sample cuvet 100 and the head portion 108*a* of the sealing stopper 108 are covered with, for example, a cap-shaped holding cover 109 made of aluminum, and the holding cover 109 is fitted on a peripheral wall of the flange portion 102 of the sample cuvet 100 to surround and hold the sealing stopper 108 from an outside. Then, for example, at the center of the holding cover 109, a hole portion 109*a* is formed so as to face the head portion 108*a* of the sealing stopper 108.

Figure 6B:
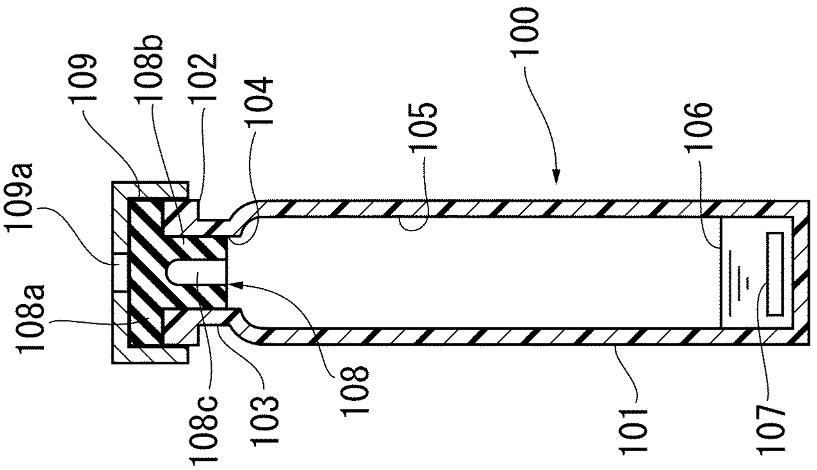
FIG. 6A is an exploded perspective view illustrating a sample cuvet used in the first embodiment and FIG. 6B is an explanatory cross-sectional view of FIG. 6A.
Figure 6A:
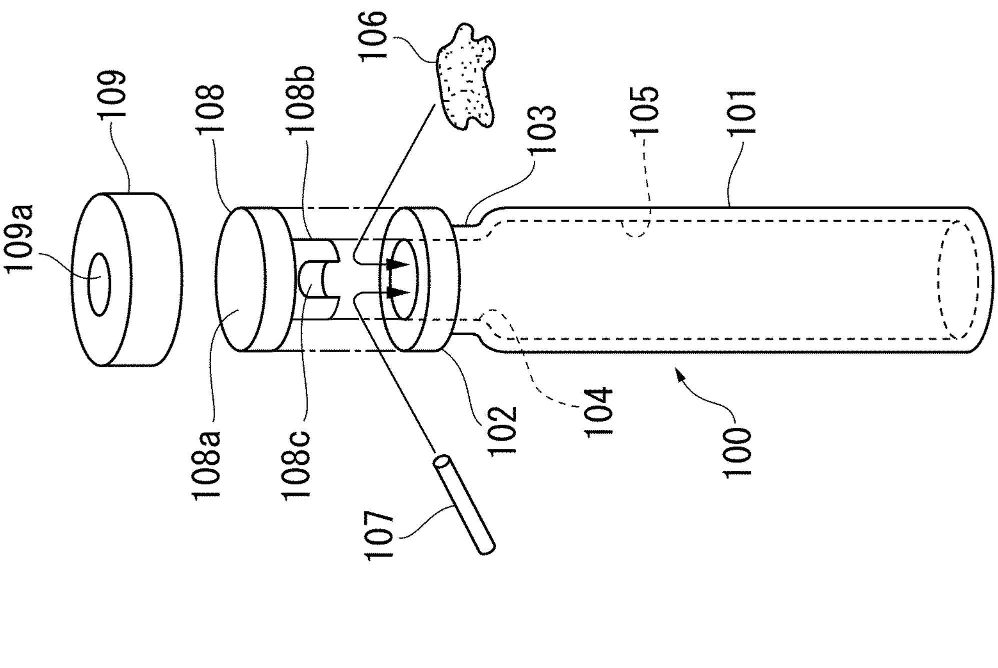

Further, as illustrated in FIGS. 6A and 6B, the sample cuvet 100 stores the reagent 106 and the stirrer bar 121 under a state in which the small diameter hole portion 104 of the cylindrical container 101 is opened, and in this state, the sealing stopper 108 seals the small diameter hole portion 104 of the cylindrical container 101, and the sealing stopper 108 is covered with the holding cover 109.

The sample cuvet 100 is supplied to a user as an accessory or a measurement kit of a gel particle measurement apparatus.

Then, as a method of introducing the sample S into the cylindrical container 101 of the sample cuvet 100 of this embodiment, for example, there is a method of perforating the sealing stopper 108 through use of the hole portion 109*a* of the holding cover 109 with a perforation tool (not shown) such as an injection needle, and injecting the sample S into the cylindrical container 101 with an injector (not shown) through the perforated hole. Further, in order to facilitate the introduction of the sample S, the sealing specification of the sealing stopper 108 may be set so that the inside of the cylindrical container 101 keeps a predetermined negative pressure level with respect to the atmospheric pressure.

Next, operation of the gel particle measurement apparatus according to this embodiment is described.

In this embodiment, as illustrated in FIG. 4, the sample S containing an endotoxin is injected into the sample cuvet 100, and a start switch (not shown) is switched on, leading to the start of a measurement sequence by the gel particle measurement apparatus.

In the measurement sequence, the stirrer bar 121 is caused to rotate by the stirring-driving device 120 to stir the mixing solution W formed of the sample S and the limulus reagent in the sample cuvet 100. Thus, the entire mixing solution W is stirred homogeneously and is inhibited from being gelated.

Further, in the measurement sequence, the mixing solution W in the sample cuvet 100 is irradiated with the coherent light Bm from the laser light source 130, a backscattered light component directed toward the laser light source 130 out of the light scattered in the mixing solution W is detected with the backscattered light detector 140, and a detection output from the backscattered light detector 140 is captured in the data analyzer 160.

On the other hand, in the mixing solution W of the sample cuvet 100, the stimulation of the endotoxin is delivered to the limulus reagent, a limulus reaction illustrated in FIG. 3 takes place, and the gel particles G are sequentially produced while the gelation of the entire mixing solution W is inhibited.

In this embodiment, a time when, for example, one gel particle G is produced in a passage area of the coherent light Bm from the laser light source 130 is grasped as a time point of the initiation of the production of the gel particle G, which leads to the timing of a phase transition point of the mixing solution W from a sol phase to a gel phase.

In the reaction process described above, the data analyzer 160, for example, as illustrated in FIG. 8, reads the detection output from the backscattered light detector 140 as scattered light quantity data (digital data), and then averaging/filtering processing is carried out to measure the variation component in the scattered light quantity data.

Next, the changing point to increase (corresponding to $P_2$ in FIG. 1C) of the scattered light quantity data detected by the backscattered light detector 140 is extracted based on the variation component in the scattered light quantity data, and the endotoxin concentration (ETX concentration) in the sample S is determined by referring to a preliminarily defined calibration curve. The result is displayed on the display 170.

The calibration curve in this example shows a relationship between the endotoxin concentration (ETX concentration) and the threshold of a time to the changing point to increase of the scattered light quantity data. The endotoxin concentration (ETX concentration) is determined based on a correlation between the time to the changing point to increase of the scattered light quantity data and the calibration curve. Further, the display 170 is switched to display data such as time-series date of the scattered light quantity data and time-series measurement data of the variation component in the scattered light quantity data, in addition to displaying the endotoxin concentration (ETX concentration).

In particular, in this embodiment, the time point of the initiation of the production of the gel particles G can be measured more quickly by devising the reagent R.

This is supported by the examples described later.

<Example of Creation of Calibration Curve>

An example of the creation of a calibration curve adopted in this embodiment is hereinafter described.

A change in the scattered light intensity (scattered light quantity data) is checked by the backscattered light detector 140 in the gel particle measurement apparatus, with respect to limulus reagents when samples having various endotoxin concentrations (for example, 10, 1, and 0.1 pg/ml) are added, defining predetermined experimental conditions, for example, as follows, using the gel particle measurement apparatus according to the first embodiment.

The experimental conditions used in this example are as follows.

Laser light source 130: red light or blue light

Backscattered light detector 140: photodiode

Number of rotations of stirrer bar 121: 1,000 rpm

Thermostatic condition: 37° C.

Figure 9A:
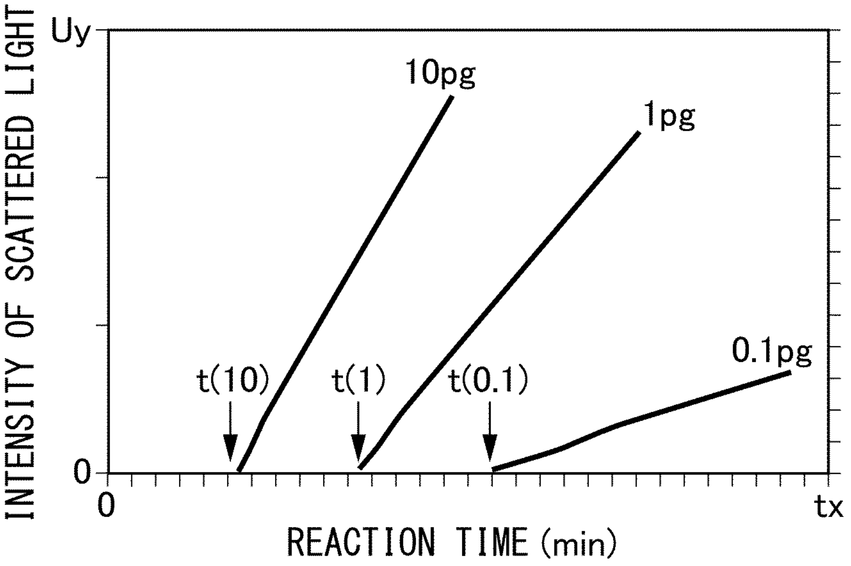
FIG. 9A is an explanatory diagram showing examples of the detection of gel particles by backscattering photometry for samples having known endotoxin concentrations and FIG. 9B is an explanatory diagram showing an example of the creation of a calibration curve with the results of FIG. 9A.

FIG. 9A is a graph prepared by plotting the values of the scattered light intensity at time course for each sample specimen of the endotoxin concentrations of 10 pg/ml, 1 pg/ml, and 0.1 pg/ml. The axis of ordinate of FIG. 9A represents scattered light intensity (maximum scattered light intensity scale in the graph is represented by Uy), and the axis of abscissa of FIG. 9A represents a reaction time (maximum reaction time scale in the graph is represented by tx [for example, 100 min]).

In the figure, any of the changes in the scattered light intensities for respective conditions shows the tendency that the portion kept at a constant level of nearly 0 increases after a certain time passes. The changing point to increase of each of the scattered light intensities corresponds to the time point of the initiation of the production of gel particles (timing of the phase transition of the sample specimen containing an endotoxin from a sol phase to a gel phase), and is estimated to mean the increase of light in amount owing to the gelation initiation time.

In order to determine the gelation initiation time, in this embodiment, in the graph of FIG. 9A, there was manually determined a point of intersection of a straight line obtained by approximating the portion in which the scattered light intensity is constant (generally, 0) and a straight line obtained by approximating a change portion in which the scattered light intensity is increasing, to thereby determine each of the gelation initiation times (reaction times) t(10), t(1), and t(0.1).

Figure 9B:
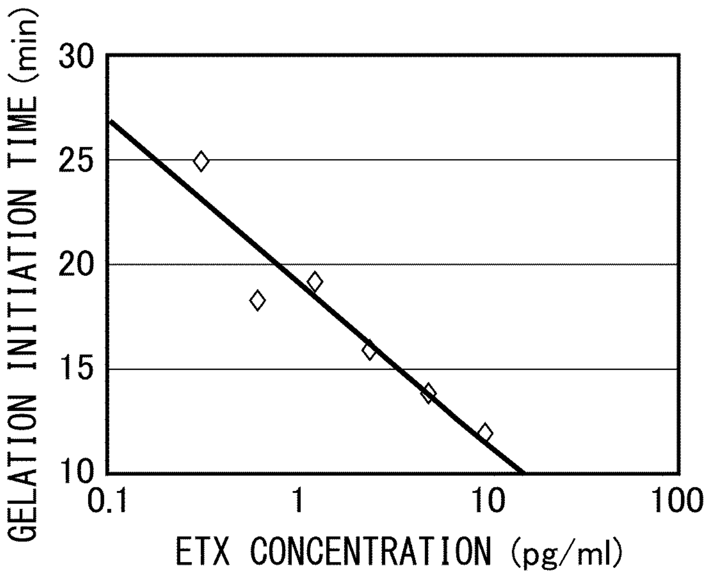

Further, in this embodiment, the values of the gelation initiation times t(10), t(1), and t(0.1), which were obtained from the graph of FIG. 9A, were used to prepare a calibration curve (see FIG. 9B).

In FIG. 9B, the calibration curve is prepared by plotting values of respective gelation initiation times, taking the ETX concentration (logarithmically converted) as the endotoxin concentration in the X-axis and taking the gelation initiation time in the Y-axis, and by drawing a straight line by a minimum square method with respect to these values. At this time, a linear relationship is obtained in the values of the gelation initiation times with respect to the sample specimen of each endotoxin concentration, and thus, a high correlation showing a correlation coefficient is exhibited.

By the way, an example of the calibration curves obtained in this embodiment is as follows.

| Endotoxin concentration (pg/ml) | Gelation initiation time (min.) |
|---|---|
| 10 pg/ml: t(10) = | 12 (min.) |
| 1 pg/ml: t(1) = | 20 (min.) |
| 0.1 pg/ml: t(0.1) = | 70 (min.) |

For comparison, the same lot of endotoxin kit which was used as above measurement (gelation reaction measurement apparatus) manufactured by Wako Pure Chemical Industries, Ltd. and adopting a turbidimetric time assay was used, and endotoxin concentrations and gelation times were investigated. The following results were provided.

| Endotoxin concentration (pg/ml) | Gelation time (min.) |
|---|---|
| 10.0 | 18.0 |
| 1.0 | 41.8 |
| 0.5 | 56.3 |
| 0.1 | 123.7 |

As described above, in this embodiment, the gel particle measurement apparatus stirs the mixing solution W formed of the sample S and the limulus reagent under a predetermined thermostatic environment, detects a backscattered light component returning to the rear of the laser light source 130 in the irradiation light Bm partially blocked and scattered due to the appearance of the gel particles G formed of coagulin particles produced in the mixing solution W, and captures the gelation initiation time.

That is, this embodiment adopts a system of detecting a backscattered light component, and is effective for grasping a time point of the initiation of the production of gel particles, as compared with other systems of detecting a scattered light component.

In this embodiment, attention is paid to a backscattered light component returning to the rear of the incident light source out of the scattered light, and the reason for this is as follows.

Figure 7A:
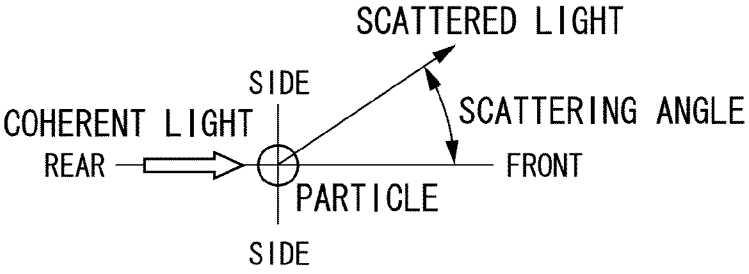
FIG. 7A is an explanatory diagram illustrating a scattering direction of scattered light when gel particles are irradiated with coherent light and FIG. 7B is an explanatory diagram illustrating a distribution of intensities of scattered light involved in a change in particle diameter of the gel particles.
Figure 7B:
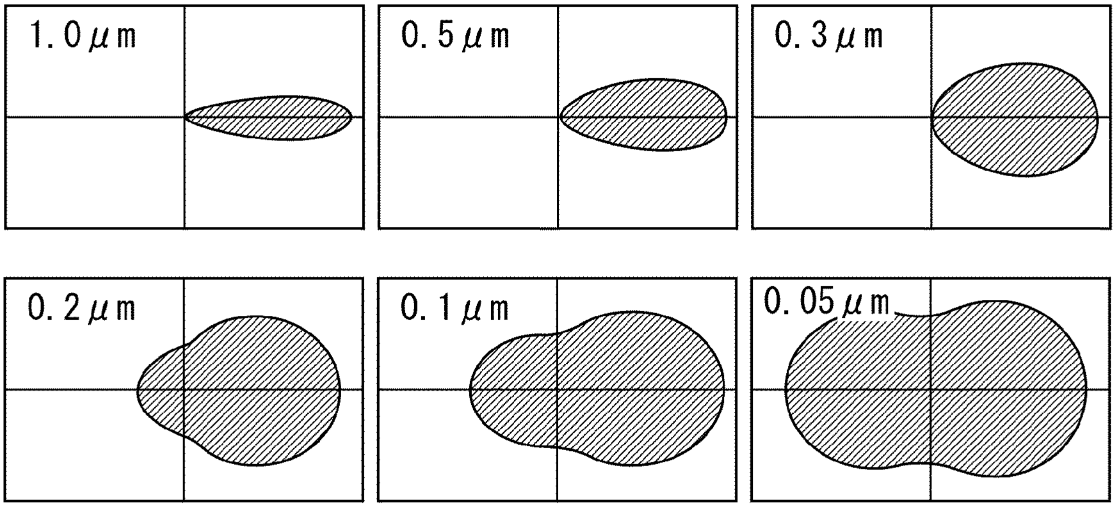

In general, as illustrated in FIG. 7A, assuming a model in which a particle is irradiated with coherent uniform light (coherent light) such as laser light, it is widely known that the coherent light is scattered due to the presence of the particle. A relationship between the size of the particle and the scattered light is examined in such a scattering phenomenon, and for example, a relationship as illustrated in FIG. 7B is observed in the intensity and directivity of the scattered light generated by the entrance of a single light beam. In FIG. 7B, the scattering phenomenon includes forward-scattering that occurs in the same direction as that of light entering the particle, side scattering that occurs in a direction orthogonal to that of the light entering the particle, and backward scattering that occurs in a direction opposite to that of the light entering the particle.

In such a scattering phenomenon, considering a particle size and a scattering direction, apart from energy to be generated, forward-scattering becomes more dominant as the particle size becomes larger, and scattering in all directions including backward scattering is observed when a particle size is small. According to such an observation result, forward-scattering is considered to be advantageous in order to capture large particles. On the other hand, in order to quickly capture small particles produced first under a phenomenon in which particles come out of nothing and grow, any direction may be suitable. However, considering that energy is small, when attenuation of scattered light in a solvent in which particles are present is considered, backward scattering with less attenuation (less absorption caused by the influence of a solvent) is considered to be suitable.

Above all, it is presumed that, in the gel particle measurement apparatus in this embodiment, the gel particle detection by backward scattering immediately after the sample cuvet is more excellent than the detection by scattering in any of the directions, for the purpose of detecting produced minute particles as quickly as possible so as to capture particles that come out of nothing (phase transition called gelation).

Accordingly, the above-mentioned timing for the phase transition is measured by adopting a detection system using backward scattering, for the purpose of quickly detecting minute particles appearing due to the phase transition by a limulus reagent with good sensitivity.

In summary, a system for detecting a backscattered light component in the scattered light generated by the appearance of minute particles is excellent in the following two points. That is, small particles can be detected quickly, and scattered light can be detected without attenuation by a solvent in which particles are floating. Further, basically, it is not necessary to set an optical path through which incident light from the incident light source passes, and hence, it is also one of the excellent points that a mechanism of the device can be further simplified.

In addition, in this example, in order to obtain high sensitivity of detection accuracy of the backscattered light detector 140, coherent strong light such as laser light is used, and in order to detect a minute change, in a change at a low concentration, stray light is removed by the stray light-removing member 150 so that scattered light except backscattered light and transmitted light directly passing through the periphery of the gel particles out of the light scattered particularly is not directed toward the backscattered light detector 140 as the stray light. Thus, only a backscattered light component scattered by the gel particles out of the irradiation light Bm from the laser light source 130 enters the backscattered light detector 140, and a change in backscattered light is correspondingly detected reliably.

In actuality, the measurement of a backscattered light change caused by backscattering detection with a model apparatus embodying the gel particle measurement apparatus according to the first embodiment provided the following results.

Measurement Example for First Embodiment

The gel particle apparatus according to the first embodiment measures the change of the backscattered light in time sequence for a specimen sample, the specimen sample being prepared by adding 10 pg/ml of a standard endotoxin to water.

Figure 10A:
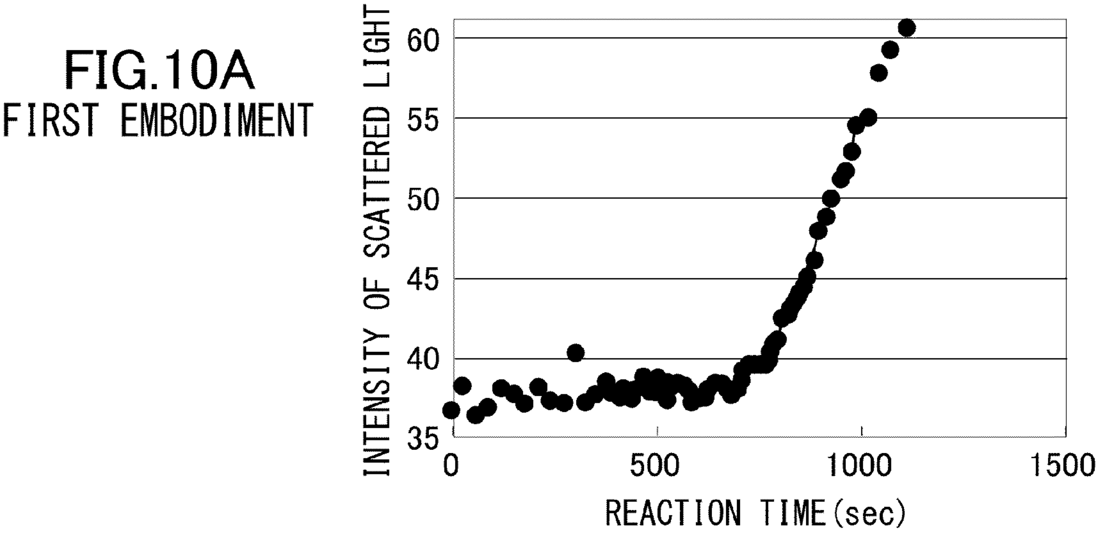
FIG. 10A is an explanatory diagram showing an example of actually measured data obtained by subjecting a water sample having a standard endotoxin added thereto to backscattering photometry with the gel particle measurement apparatus according to the first embodiment.

FIG. 10A shows the results. It should be noted that the axis of ordinate of the figure indicates a relative scattered light intensity and the axis of abscissa thereof indicates a time (sec.).

Measurement Example for First Comparative Embodiment

A gel particle measurement apparatus according to a first comparative embodiment (embodiment in which a forward-scattering detector for detecting forward-scattered light traveling toward a front opposite to the backscattered light is used) measures the change of the forward-scattered light traveling toward the front opposite to the backscattered light in time sequence for the same specimen sample as the specimen sample used in the first embodiment 1.

Figure 10B:
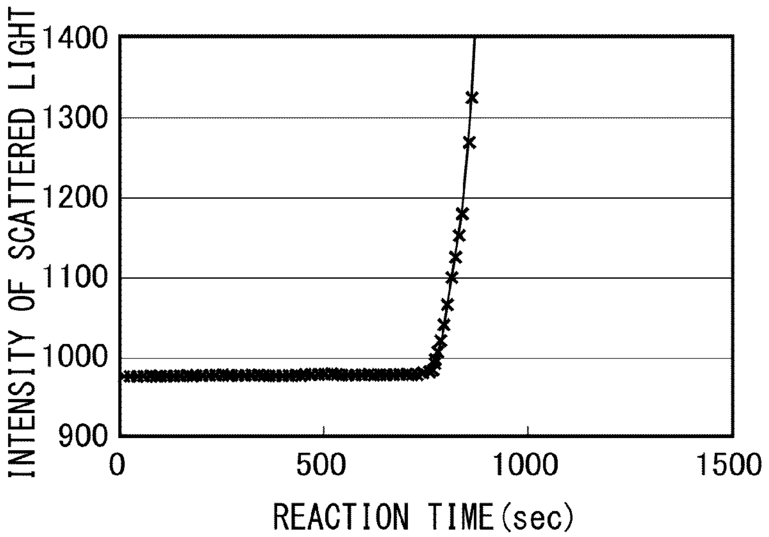
FIG. 10B is an explanatory diagram showing an example of actually measured data obtained by subjecting a water sample having a standard endotoxin added thereto, which is similar to that of FIG. 10A, to forward-scattering photometry with a gel particle measurement apparatus according to a first comparative embodiment.

FIG. 10B shows the results. It should be noted that the axis of ordinate of the figure indicates a relative scattered light intensity and the axis of abscissa thereof indicates a time (sec.).

Measurement Example for Second Comparative Embodiment

A gel particle measurement apparatus according to a second comparative embodiment (embodiment in which a transmitted light detector for detecting transmitted light traveling toward a front opposite to the backscattered light is used) measures the change of transmitted light (including the forward-scattered light in this example) traveling toward the front opposite to the backscattered light in time sequence for the specimen sample used in the first embodiment.

Figure 10C:
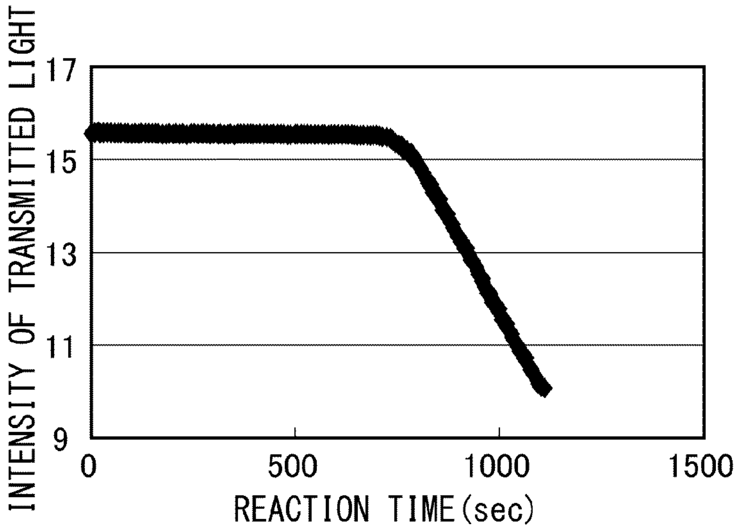
FIG. 10C is an explanatory diagram showing an example of actually measured data obtained by irradiating a water sample having a standard endotoxin added thereto, which is similar to that of FIG. 10A, with forward-transmitted light through use of a gel particle measurement apparatus according to a second comparative embodiment.

FIG. 10C shows the results. It should be noted that the axis of ordinate of the figure indicates a transmitted light intensity and the axis of abscissa thereof indicates a time (sec.).

<Comparison Between First Embodiment and First and Second Comparative Embodiments>

When the first embodiment is compared with the first comparative embodiment, compared with the timing of the phase transition of a specimen sample based on a reduction in transmitted light in the second comparative embodiment, any gelation initiation time (increase change point of the scattered light intensity) corresponding to the timing of the phase transition of a specimen sample by forward-scattered light according to the first comparative embodiment tends to be delayed (about 10 to 40 seconds) in detection start from a gelation initiation time (increase change point of the scattered light intensity) corresponding to the timing of the phase transition in a specimen sample by backscattered light according to the first embodiment.

Thus, the superiority (promptness) of backscattering detection is significant at a low endotoxin concentration.

Modification

Figure 11A:
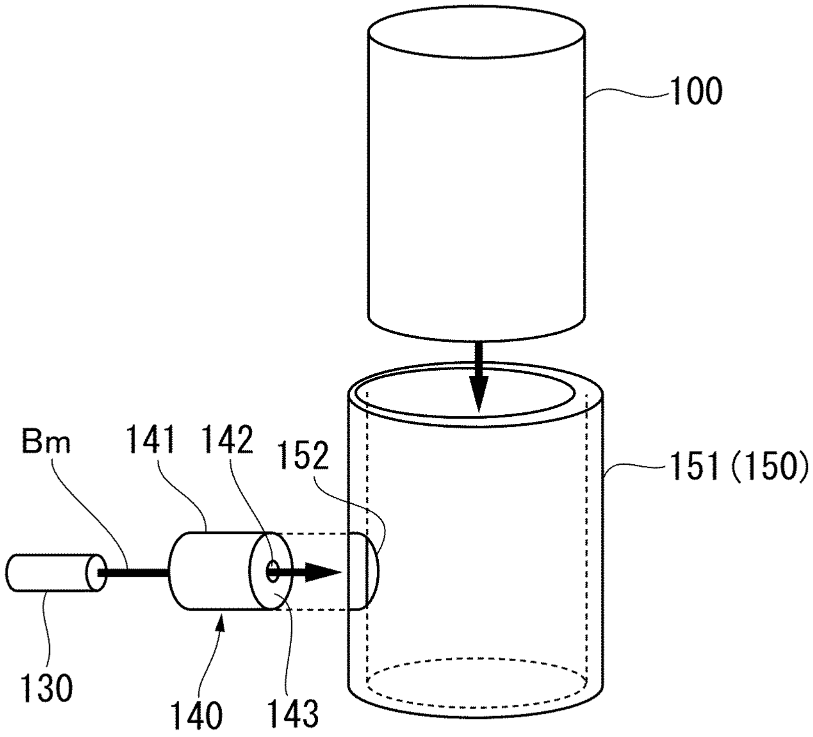
FIGS. 11A and 11B are each an explanatory diagram illustrating a modification of the gel particle measurement apparatus according to the first embodiment.

In this embodiment, the stray light-removing member 150 is arranged outside the sample cuvet 100 and on an opposite side of the laser light source 130 with respect to the sample cuvet 100. However, the present invention is not limited thereto. For example, as illustrated in FIG. 11A, a tubular cover 151 may be set so as to surround the periphery of the sample cuvet 100, the inner surface of the tubular cover 151 may be covered with, for example, a black light absorbing member and a fitting hole 152 for mounting the backscattered light detector 140 may be opened in a part of the tubular cover 151, the backscattered light detector 140 may be mounted through the fitting hole 152, and the irradiation light Bm from the laser light source 130 may be allowed to pass through the passage hole 142 of the backscattered light detector 140.

Further, in this embodiment, although the sample cuvet 100 is formed of a transmissive material, transmission of light in the mixing solution W in the sample cuvet 100 is hardly required. Therefore, as long as part of the sample cuvet 100 corresponding to setting positions of the laser light source 130 and the backscattered light detector 140 is set as an incident portion having transmissive property, the other parts of the sample cuvet 100 may be formed of a non-transmissive material or may be coated with a non-transmissive coating.

Figure 11B:
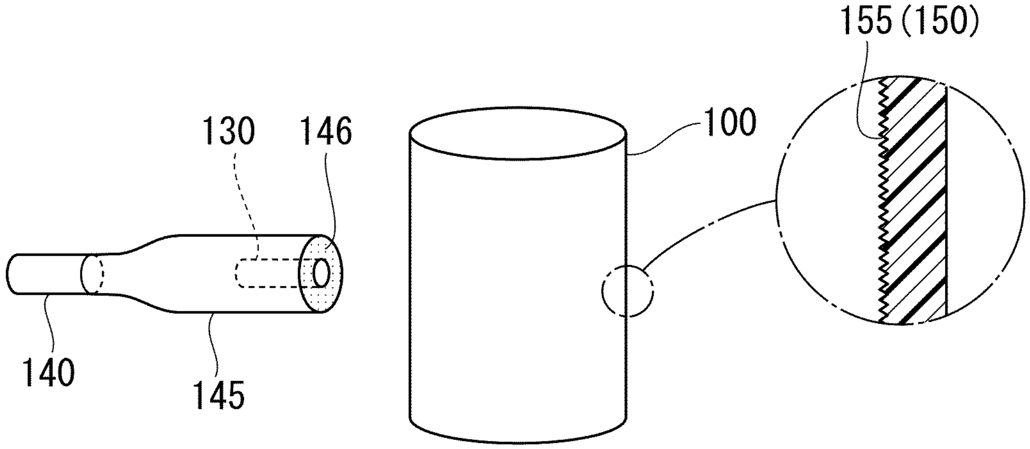

Further, in this embodiment, although the laser light source 130 and the backscattered light detector 140 are configured as separate units, for example, as illustrated in FIG. 11B, a number of light-transmissive glass fibers 145 as a light guiding member may be bound so as to surround the periphery of the laser light source 130, one end of each glass fiber 145 on the sample cuvet 100 side may be allowed to function as a light introduction surface 146, the backscattered light detector 140 may be provided so that a detection surface is placed so as to be opposed to the other end of each glass fiber 145, and an optical detection unit may be configured integrally, using the laser light source 130, the backscattered light detector 140, and the glass fibers 145 as a light guiding member.

Further, the stray light-removing member 150 is not limited to a form in which the stray light-removing member 150 is provided outside the sample cuvet 100. For example, as illustrated in FIG. 11B, a minute rough surface 155 may be formed on an inner wall circumferential surface of the sample cuvet 100 as the stray light-removing member 150, and a stray light component out of the irradiation light emitted from the laser light source 130 may be randomly reflected from the minute rough surface 155 to be attenuated.

It should be noted that although the stray light-removing member 150 is provided in this embodiment, it is not necessarily required to use the stray light-removing member 150. For example, the degree of influence of a stray light component may be actually measured in advance through use of a sample specimen having a known endotoxin concentration, and based on the actually measured value, for example, the stray light component actually measured from a detection output from the backscattered light detector 140 may be corrected.

Further, in this embodiment, the gel particle measurement apparatus with respect to the sample cuvet 100 for one analyte (sample S) is shown. However, under a request that a plurality of analytes (samples) be treated simultaneously, for example, a multi-sample cuvet in which a plurality of sample cuvets 100 are integrated may be prepared and the laser light source 130 and the backscattered light detector 140 may be arranged correspondingly to each sample cuvet so that a plurality of analytes (samples) can be measured simultaneously.

Further, although the first embodiment discloses that a substance to be measured is an endotoxin, the present invention is not limited thereto. For example, a substance to be measured may be a β-D-glucan, using the same measurement hardware and the same or similar limulus reagent.

Second Embodiment

FIG. 12 illustrates main portions of a gel particle measurement apparatus according to a second embodiment to which the present invention is applied. It should be noted that the same constituent elements as those of the first embodiment are denoted by the same reference symbols as those in the first embodiment, and the detailed description thereof is omitted.

In the figure, substantially in the same way as in the first embodiment, the gel particle measurement apparatus includes the laser light source 130 outside the sample cuvet 100, and the backscattered light detector 140 is set on the same side as the laser light source 130. Unlike the first embodiment, however, for example, a transmitted light detector 180 is set outside the sample cuvet 100 and on an opposite side of the laser light source 130 with respect to the sample cuvet 100, the detection output of the transmitted light detector 180 is captured in the data analyzer 160, a time point of the initiation of the production of gel particles is determined in the same way as in the first embodiment based on the detection output of the transmitted light detector 180.

In this example, the transmitted light detector 180 has a detection surface capable of detecting a light flux region from the laser light source Bm, and the detection accuracy of the transmitted light detector 180 is set so that the detector can detect a change in quantity of transmitted light caused by the presence or absence of the one to several gel particles G present in the area which transmitted light Bm passes.

Further, in this embodiment, a deflection filter 190 is provided between the sample cuvet 100 and the transmitted light detector 180. The deflection filter 190 removes stray light as a component of the scattered light scattered by the gel particles G produced in the mixing solution W, the component traveling toward the transmitted light detector 180, out of the irradiation light Bm from the laser light source 130. The principle of the removal of the stray light by the deflection filter 190 is as described below. When the coherent light Bm from the laser light source 130 is scattered by the gel particles G, the phase of the scattered light shifts. The stray light component of a phase component except the phase of the transmitted light Bm is cut off by utilizing the foregoing fact.

In addition, when such deflection filter 190 is not used, the transmitted light detector 180 detects a transmitted light component including a scattered light component. The transmitted light component may be analyzed on the side of the data analyzer 160 in consideration of the fact that the scattered light component is included. Alternatively, the transmitted light component may be analyzed on the side of the data analyzer 160 after such correction that the scattered light component is removed has been performed.

Although a system involving detecting the transmitted light in the transmitted light detector 180 is adopted in this embodiment, a scattered light detector may be used instead of the transmitted light detector 180. Further, the position at which the scattered light detector is placed is not limited to the opposite side of the sample cuvet 100 with respect to the laser light source 130, and the detector may be placed at any site as long as the site is different from that of the laser light source 130. For example, when the detector is placed at a site deflected by 90° in the circumferential direction of the sample cuvet 100 with respect to the laser light source 130, the detector can detect side-scattered light.

Next, the operation of the gel particle measurement apparatus according to this embodiment is described.

Figure 12A:
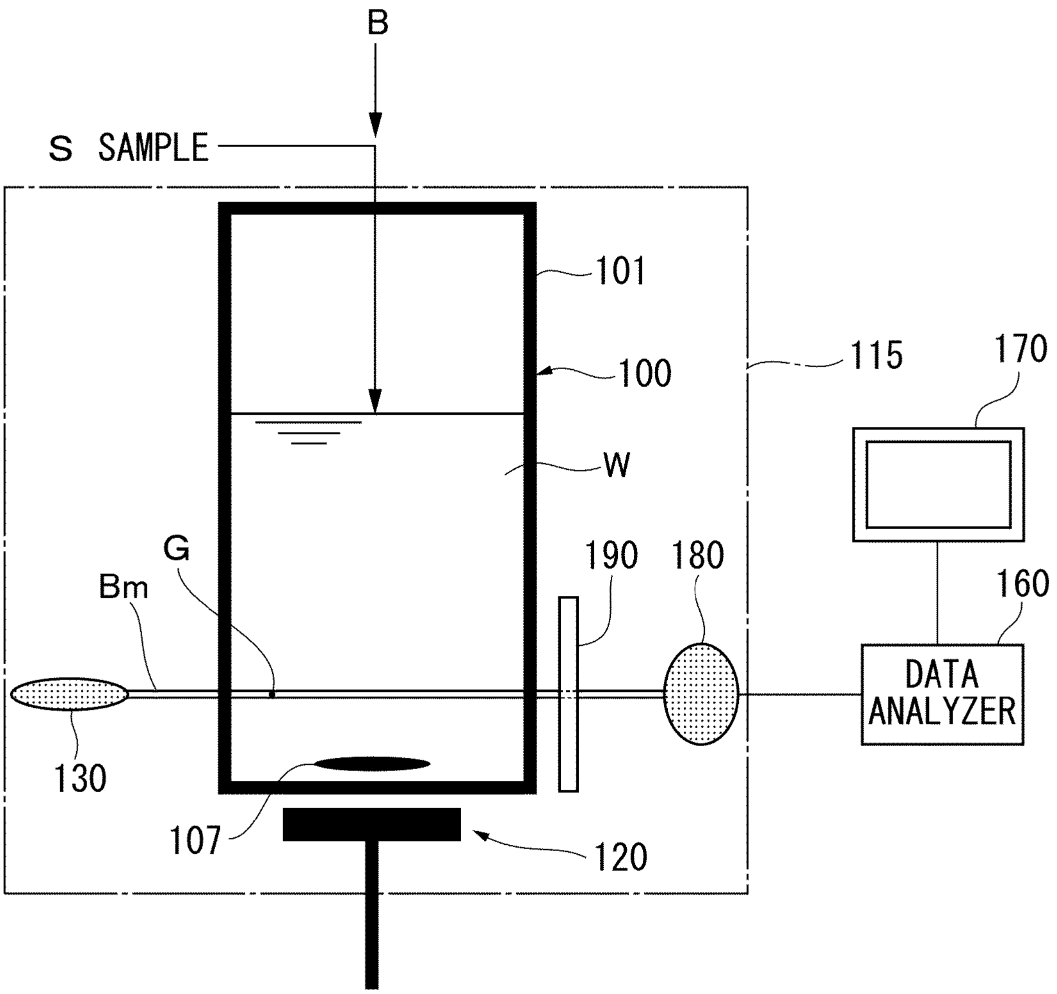
FIG. 12A is an explanatory diagram illustrating a gel particle measurement apparatus according to a second embodiment of the present invention and FIG. 12B is an arrow view viewed from a direction B in FIG. 12A.
Figure 12B:
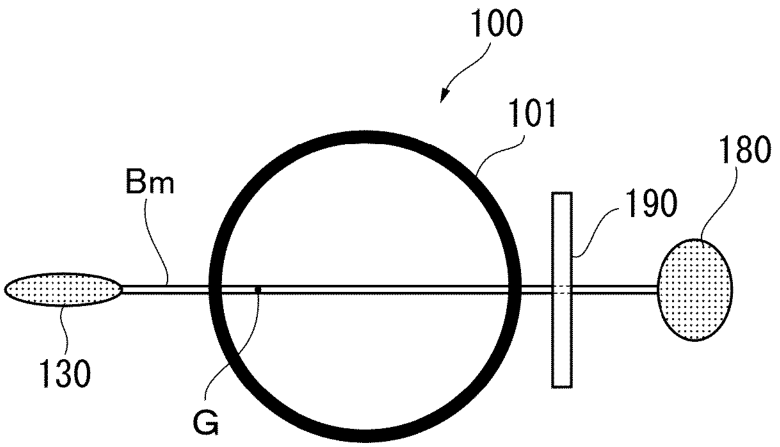

In this embodiment, when the sample S containing the endotoxin is injected into the sample cuvet 100, in which the reagent R (in this example, a product obtained by adding the same particle formation accelerating factor as that of the first embodiment to the limulus reagent) has been stored in advance, as illustrated in FIGS. 12A and 12B, and then the operation of turning on a start switch (not shown) is performed, a measurement sequence by the gel particle measurement apparatus is initiated.

In the measurement sequence, a stirrer bar 107 is rotated by a stirring-driving device 120 to stir the mixing solution W formed of the sample S and the reagent R in the sample cuvet 100. Accordingly, the entirety of the mixing solution W is homogeneously stirred and the gelation of the entirety of the mixing solution W is suppressed.

Further, in the measurement sequence, the irradiation light Bm is applied from the laser light source 130 and then the transmitted light Bm that has passed the mixing solution W in the sample cuvet 100 is detected by the transmitted light detector 180. In addition, the detection output of the transmitted light detector 180 is captured in the data analyzer 160.

Meanwhile, in the sample cuvet 100, the stimulus of the endotoxin propagates to the limulus reagent to cause such limulus reaction as illustrated in FIG. 3, and then the gel particles G are sequentially produced in a state where the gelation of the entirety of the mixing solution W is suppressed.

In this embodiment, the timing at which, for example, the one gel particle G is produced in the area which the irradiation light Bm from the laser light source 130 passes is grasped as the point of the initiation of the production of the gel particles G, and serves as the attenuation change point of the transmitted light Bm or the timing of the appearance of the scattered light.

Figure 13:
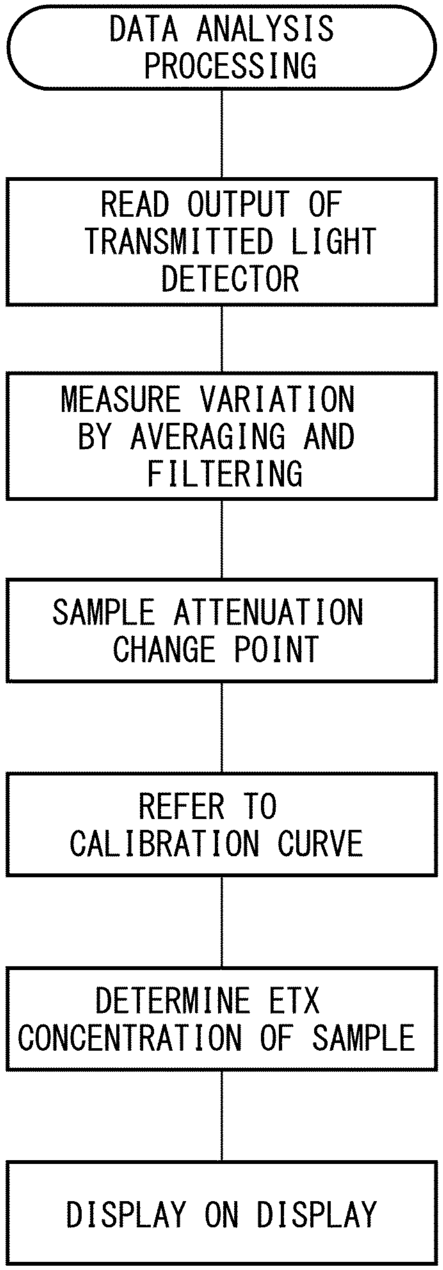
FIG. 13 is a flow chart illustrating an example of the data analysis processing of the gel particle measurement apparatus according to the second embodiment.

In such reaction process, as illustrated in, for example, FIG. 13, the data analyzer 160 reads the detection output from the transmitted light detector 180 as transmitted light quantity data (digital data), and then performs averaging/filtering processing to measure the variation component of the transmitted light quantity data.

Next, the detector samples the attenuation change point of the transmitted light Bm (corresponding to $P_2$ of FIG. 10) on the basis of the variation component of the transmitted light quantity data, determines the endotoxin concentration (ETX concentration) of the sample S with reference to a calibration curve specified in advance, and displays the concentration on a display 170.

The calibration curve in this example shows a relationship between the endotoxin concentration (ETX concentration)

and the threshold of a time to the attenuation change point of the transmitted light Bm. The endotoxin concentration (ETX concentration) is determined based on a correlation between the time to the attenuation change point of the transmitted light Bm and the calibration curve. Further, the display 170 is switched to display data such as time-series data of the transmitted light quantity data and time-series measurement data of the variation component in the transmitted light quantity data, in addition to displaying the endotoxin concentration (ETX concentration).

It should be noted that a method of creating the calibration curve is described later.

As described above, in this embodiment, the gel particle measurement apparatus attempts to grasp the timing of the initiation of the gelation by: stirring the mixing solution W formed of the sample S and the reagent R (limulus reagent+particle formation accelerating factor) under a predetermined isothermal environment; and detecting extinction resulting from the blocking of part of the transmitted light Bm by the appearance of the gel particles G formed of coagulin particles produced in the mixing solution W or the scattered light.

In particular, in this example, coherent, intense light, i.e., laser light is utilized for improving the detection accuracy of the transmitted light detector 180. In addition, in order that a minute change may be detected, the deflection filter 190 removes a stray light component by utilizing the fact that particularly in the case of a change at a low concentration, scattered stray light impinges on the gel particles G formed of coagulin particles to undergo a phase shift. Accordingly, only the transmitted light component from the laser light source 130 is incident on the transmitted light detector 180, which results in proportionately high accuracy with which the change of the transmitted light is detected.

An example of the creation of a calibration curve adopted in this embodiment is described.

The experimental conditions in this example are as follows.

Laser light source 130: red light or blue light

Transmitted light detector 180: photodiode

Number of rotations of stirrer bar 107: 1,000 rpm

Thermostatic condition: 37° C.

In this example, the reagent R (limulus reagent+particle formation accelerating factor) to which the endotoxin has been added at any one of the various concentrations (10, 1, and 0.1 pg/ml) is examined for a change in transmitted light intensity with the gel particle measurement apparatus.

Figure 14A:
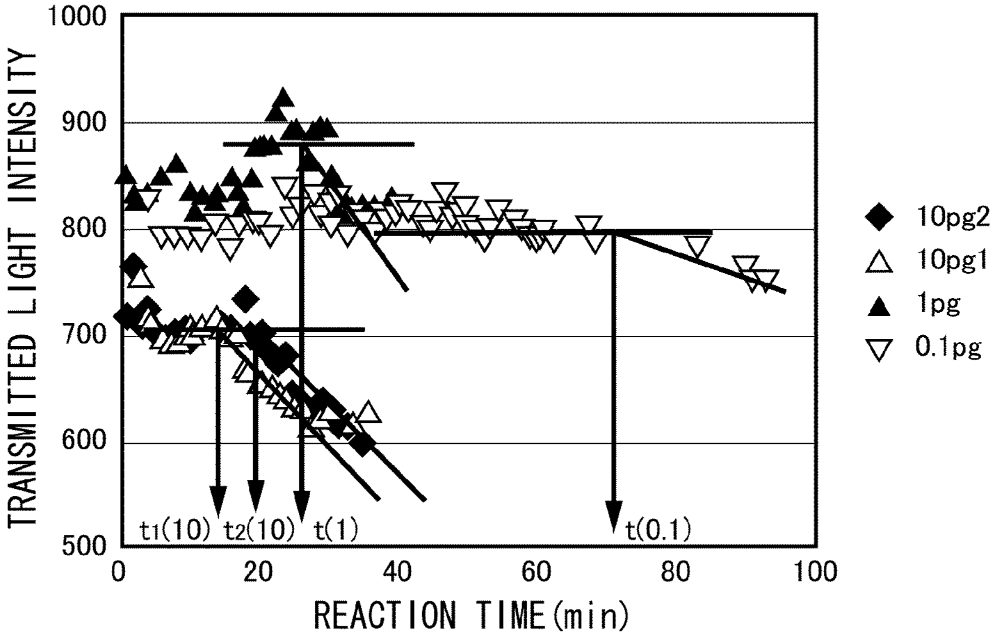
FIG. 14A is an explanatory diagram showing examples of the detection of gel particles by transmission photometry for samples having known endotoxin concentrations and FIG. 14 B is an explanatory diagram showing an example of the creation of a calibration curve with the results of FIG. 14A.

FIG. 14A shows transmitted light intensities plotted against an elapsed time for each of the concentrations, i.e., 10 pg/ml (the measurement is performed twice), 1 pg/ml, and 0.1 pg/ml.

In the figure, the change of the transmitted light intensity under each condition shows such a tendency that a portion maintaining a substantially constant level attenuates and reduces at a certain time. The attenuation change point of the transmitted light intensity corresponds to the point of the initiation of the production of the gel particles (gelation initiation time) and is assumed to mean extinction caused by the initiation of the gelation.

In order that the gelation initiation time may be determined, in this example, in the graph of FIG. 14A, a point of intersection of a straight line obtained by approximating a portion having the constant transmitted light intensity and a straight line obtained by approximating a change portion where the transmitted light intensity attenuates and inclines is manually determined, and then gelation initiation times (reaction times) t1(10), t2(10), t(1), and t(0.1) are determined for the respective concentrations.

In this example, the following results were provided.

10 pg/ml: t1(10)=16 (min.)

t2(10)=19 (min.)

1 pg/ml: t(1)=28 (min.)

0.1 pg/ml: t(0.1)=70 (min.)

Figure 14B:
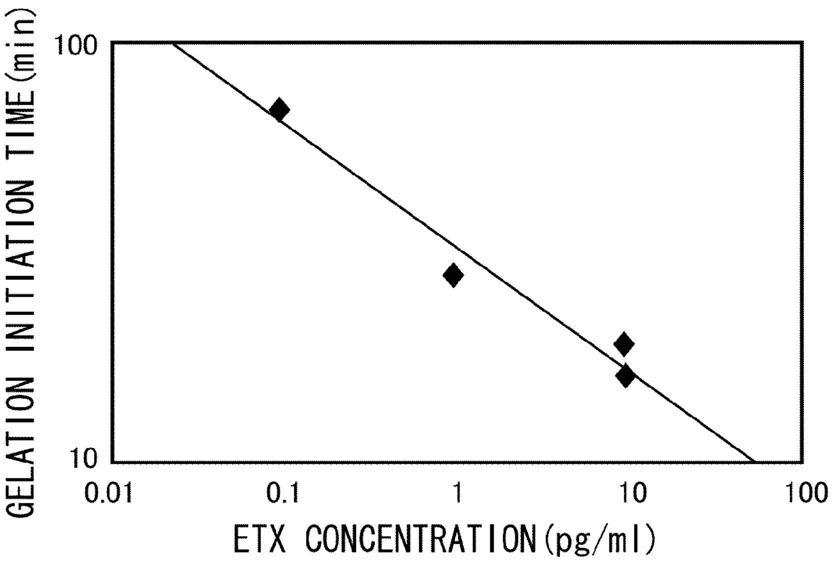

In addition, in this example, the calibration curve is created with the values for the gelation initiation times t1(10), t2(10), t(1), and t(0.1) determined from the graph of FIG. 14A (see FIG. 14B).

The calibration curve of this example provides a linear relationship when its X-axis is caused to indicate the ETX concentration (subjected to logarithmic transformation) as the endotoxin concentration and its Y-axis is caused to indicate the gelation initiation time (subjected to logarithmic transformation), and shows a high correlation having a correlation coefficient of −0.9804. Accordingly, the usefulness of the calibration curve is proved.

EXAMPLES

Example 1

FIG. 15 to FIG. 18

In Example 1, an inactive plasma protein as the particle formation accelerating factor of a gel particle measurement reagent was examined for its influence.

Specifically, the endotoxin of a sample specimen was diluted with a plasma having no endotoxin activity. In this example, a solution containing 10 pg/ml of the endotoxin was prepared with each of 100% to 1% plasmas. The solution was diluted ten-fold with 0.02% Triton-X100 water and then heat-treated (at 70° C. for 10 minutes). The solution was further diluted ten-fold at the time of measurement.

Then, the time point of the initiation of the production of gel particles was determined by subjecting each of the solutions satisfying the following conditions to measurement with the gel particle measurement apparatus according to the first embodiment: their final plasma concentrations were 0.2%, 0.1%, 0%, 10%, 5%, 1%, and 0.5%. In addition, a distribution in each particle size of products leading to the gel particles in the production process of the gel particles under each condition was measured with a particle distribution measurement apparatus. Here, an aggregometer for detecting a particle on the basis of side scattering (manufactured by Kowa Company, Ltd.) was used as the particle distribution measurement apparatus.

Figure 15A:
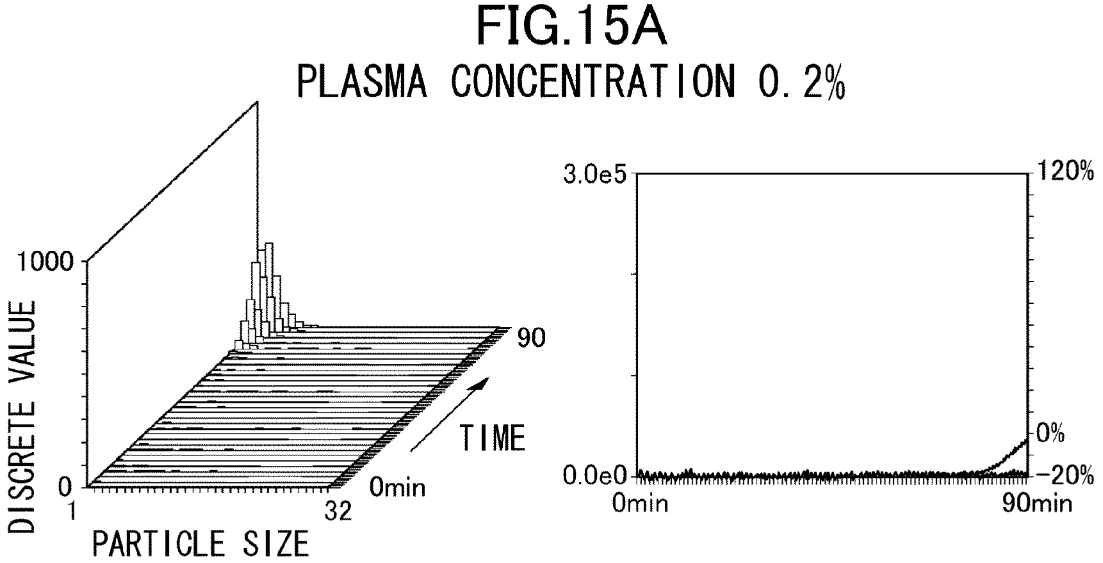
FIGS. 15A to 15C are each an explanatory diagram (1) showing the production process of gel particles when, in an embodiment in which plasma thermally denatured in the absence of an endotoxin is utilized as a particle formation accelerating factor in Example 1, the concentration of the plasma with respect to the same endotoxin concentration (10 pg/ml) is changed, FIG. 15A showing the case where the plasma concentration is 0.2%, FIG. 15B showing the case where the plasma concentration is 0.1%, and FIG. 15C showing the case where the plasma concentration is 0%.
Figure 15B:
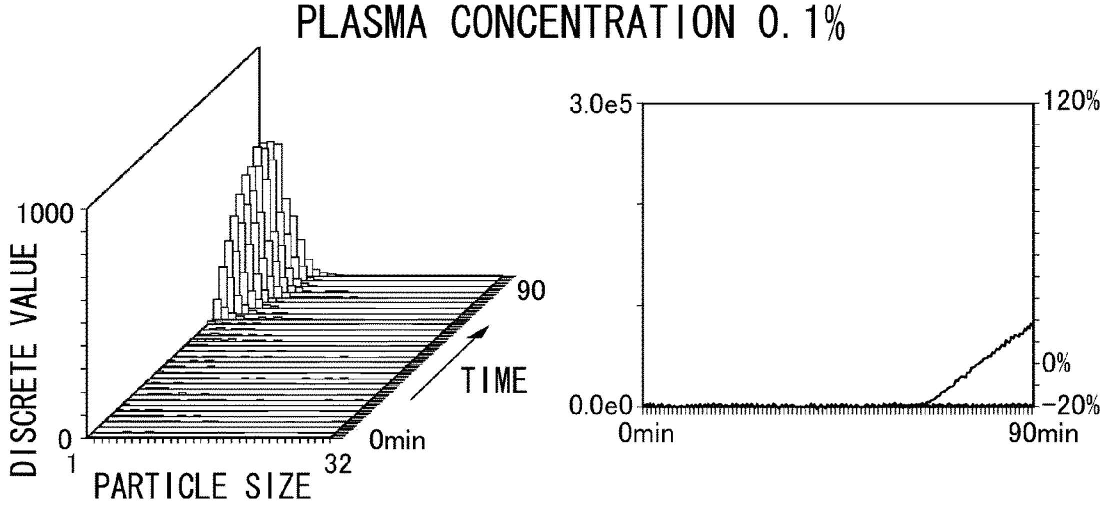
Figure 15C:
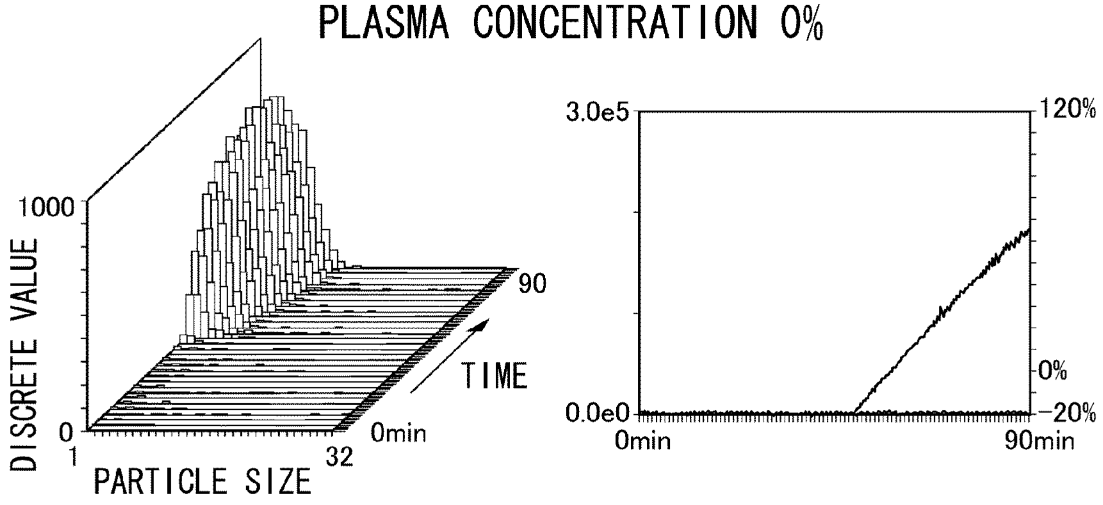
Figure 16A:
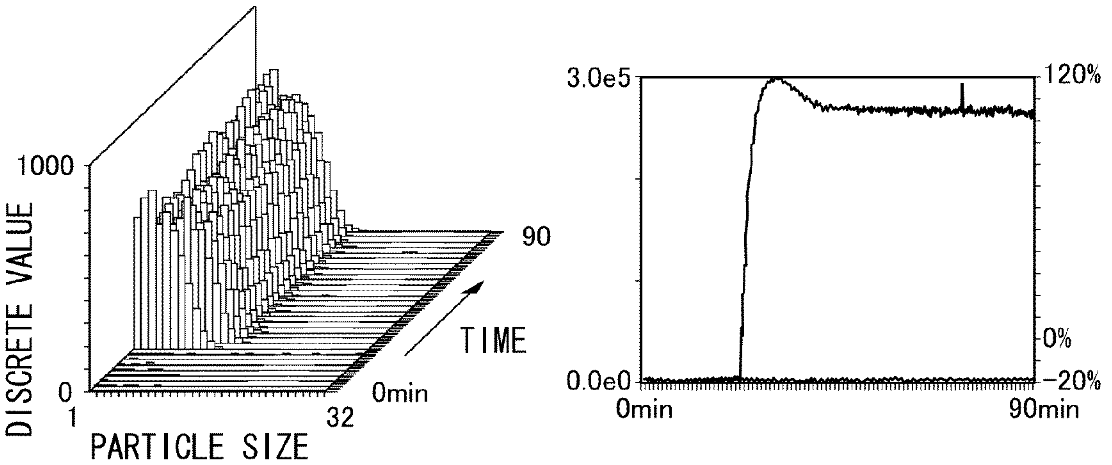
FIGS. 16A and 16B are each an explanatory diagram (2) showing the production process of the gel particles when, in the embodiment in which the plasma thermally denatured in the absence of an endotoxin is utilized as a particle formation accelerating factor in Example 1, the concentration of the plasma with respect to the same endotoxin concentration (10 pg/ml) is changed, FIG. 16A showing the case where the plasma concentration is 10% and FIG. 16B showing the case where the plasma concentration is 5%.
Figure 16B:
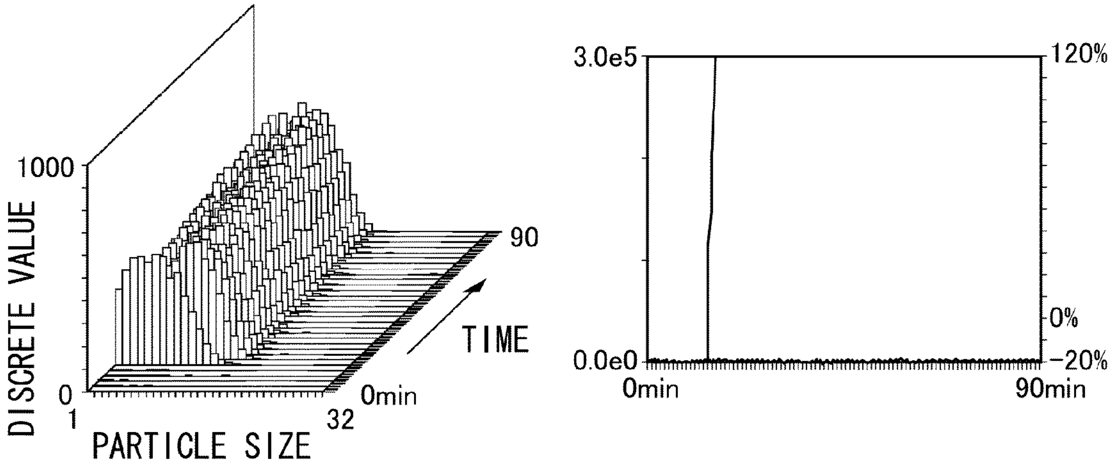
Figure 17A:
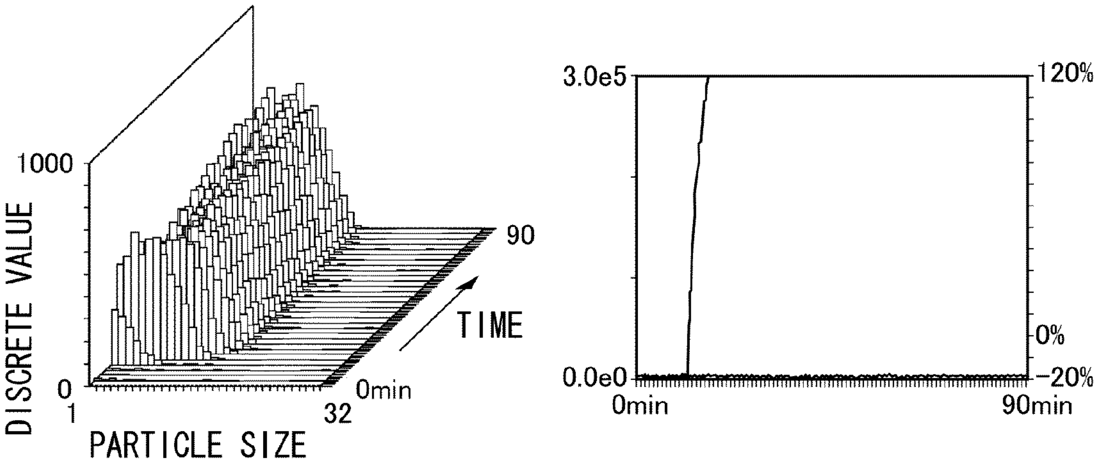
FIGS. 17A and 17B are each an explanatory diagram (3) showing the production process of the gel particles when, in the embodiment in which the plasma thermally denatured in the absence of an endotoxin is utilized as a particle formation accelerating factor in Example 1, the concentration of the plasma with respect to the same endotoxin concentration (10 pg/ml) is changed, FIG. 17A showing the case where the plasma concentration is 1% and FIG. 17B showing the case where the plasma concentration is 0.5%.
Figure 17B:
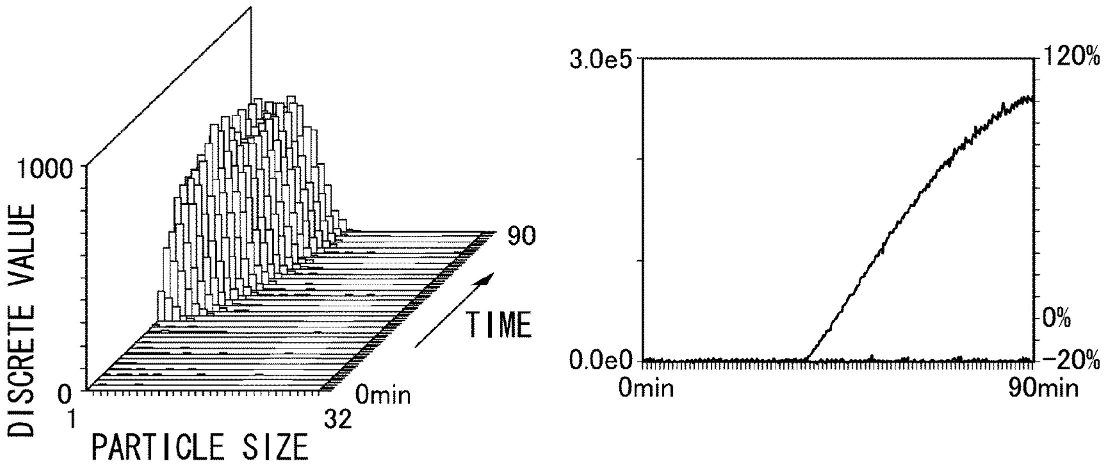

FIG. 15 to FIG. 17 show the results.

In the figures, a three-dimensional graph on the left column of each figure is obtained by classifying the particle sizes into levels 1 to 32 and counting the number of particles corresponding to each level with a lapse of time. In addition, a graph on the right column of each figure shows the total of the numbers of particles of the three-dimensional graph on the left column for each of a small size (levels 1 to 15), a middle size (levels 15 to 23), and a large size (levels 24 to 32) together with an elapsed time, and shows a chronological turbidity change (-X-).

Figure 18:
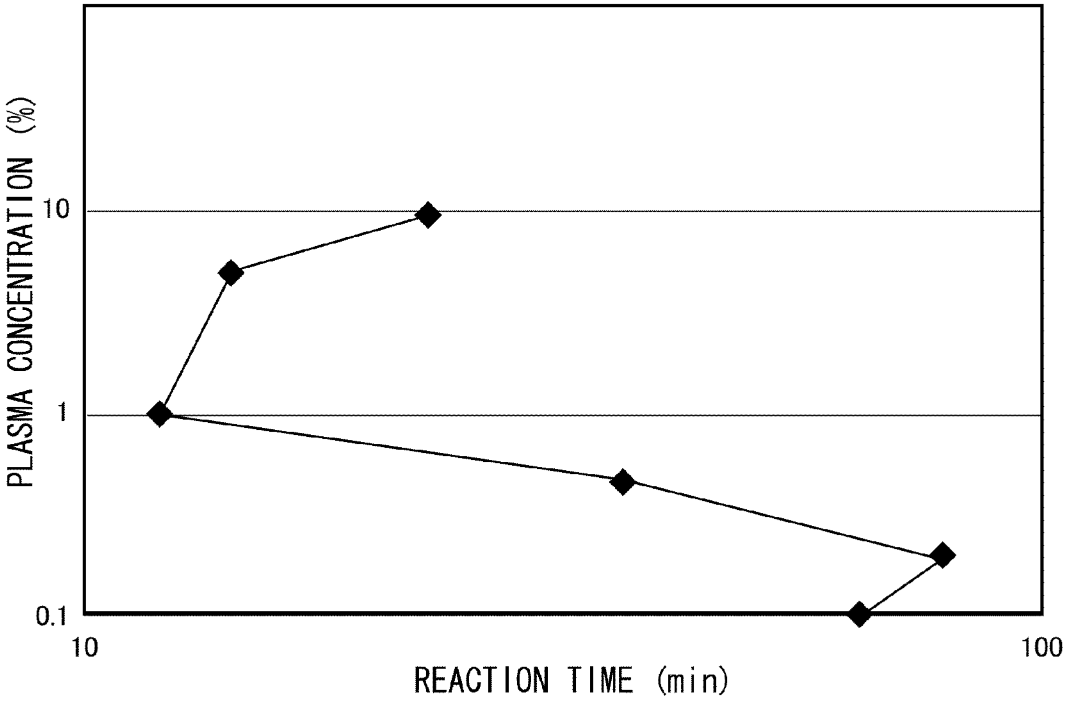
FIG. 18 is a graph chart showing a relationship between a thermally denatured plasma protein concentration with respect to the same endotoxin concentration (10 pg/ml) and a reaction time till the initiation of the production of the gel particles in FIG. 15 to FIG. 17.

In addition, FIG. 18 shows a relationship between the plasma concentration under each of the conditions shown in FIG. 15 to FIG. 17 and a reaction time till the time point of the initiation of the production of the gel particles.

According to FIG. 15 to FIG. 17 and FIG. 18, the following results are grasped.

(1) It was confirmed that the gel particle formation of Example 1 in agitating condition varied depending on the concentration of the coexistent plasma, though it was initially assumed that the reaction times till the time point of the initiation of the production of the gel particles became the same because the solutions originally contained the same endotoxin. It is understood from the foregoing that the plasma concentration affects the reaction time.

(2) It was confirmed that in this example, the reaction time till the time point of the initiation of the production of the gel particles became shortest in the case where the final plasma concentration was 1% with respect to the sample specimens having the same endotoxin concentration, and the reaction was inhibited in the case where the final concentration was 10% as compared with the foregoing case.

(3) According to FIG. 15 to FIG. 17, the following tendency is observed. While formed particles are minute or nonuniform in the sample free of any plasma, the heat-treated plasma accelerates the formation of particles having a certain size. In this example, the tendency was observed when the plasma concentration was 10% to 1%. In addition, the appearance of the gel particles was detected most quickly in the case of the thermally denatured plasma having the final concentration of 1% with respect to the same endotoxin concentration (FIG. 18). Something out of the thermally denatured plasma component may accelerate the formation of the particles. It should be noted that even when the concentration of the plasma is 1%, the concentration of an effective component may be one tenth to one several tenths of the concentration in consideration of the concentration of the plasma protein and the 100-fold dilution.

Example 2

Figure 19:
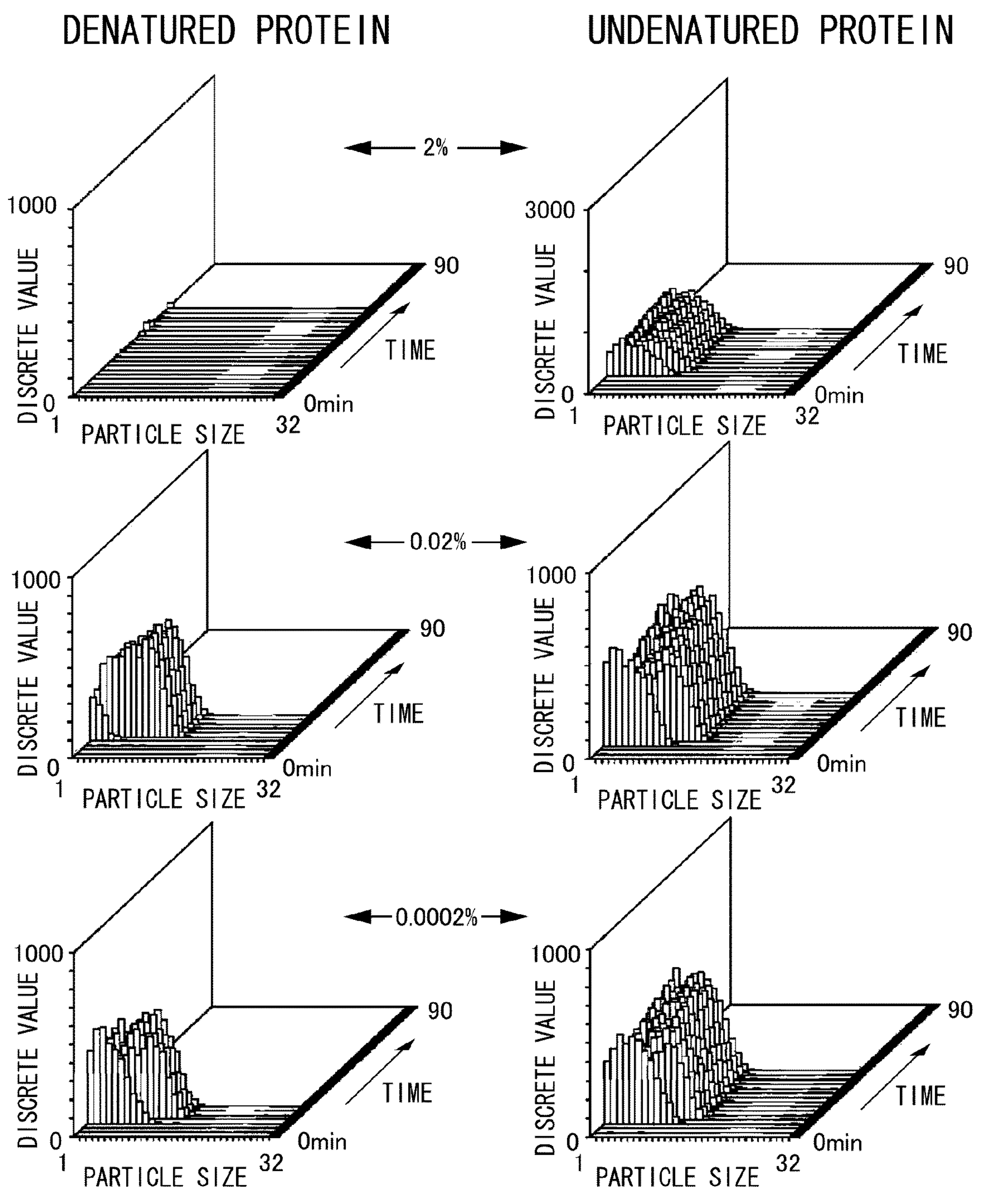
FIG. 19 are explanatory diagrams showing the production processes of gel particles when a concentration is changed for Example 2 in which a denatured protein as a particle formation accelerating factor is added to a gel particle measurement reagent and a comparative example in which an undenatured protein is added to the gel particle measurement reagent instead of the denatured protein of Example 2.
Figure 20:
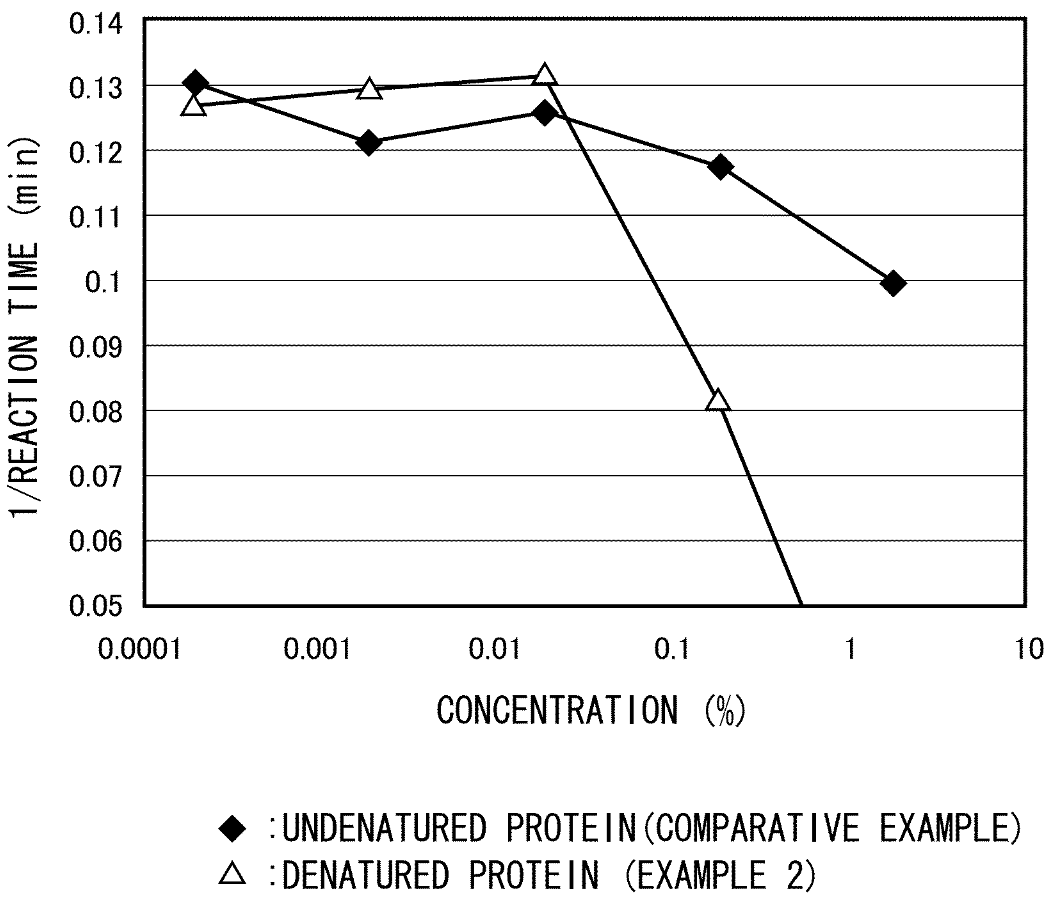
FIG. 20 is a graph chart showing a relationship between the concentration of the denatured protein or the undenatured protein and a reaction time till the production of the gel particles for each of Example 2 and the comparative example.

FIG. 19 and FIG. 20

In Example 1, the influence of the thermally denatured plasma was observed. An investigation was conducted to elucidate something effective in a plasma component, and as a result, several components including an albumin were investigated. In Example 2, a denatured protein (thermally denatured protein) was used as the particle formation accelerating factor of a gel particle measurement reagent, and in a comparative example, an undenatured protein was used instead of the denatured protein.

A sample containing an endotoxin at a predetermined concentration was subjected to gel particle measurement with each of the gel particle measurement reagents of Example 2 and the comparative example by using the gel particle measurement apparatus according to the first embodiment.

At this time, while the concentration of the denatured protein or the undenatured protein with respect to samples having the same endotoxin concentration was changed to 2%, 0.02%, or 0.0002%, the samples were subjected to a reaction by a limulus reagent under the respective conditions.

FIG. 19 and FIG. 20 show the results.

In FIG. 19, a distribution in each particle size of products leading to the gel particles in the production process of the gel particles under each condition was measured with a particle distribution measurement apparatus. The excess amount of denatured protein inhibits to make a gel particle formation, and undenatured plasma did not affect to stimulate a gel particle formation. Here, the same apparatus as that of Example 1 was used as the particle distribution measurement apparatus.

In addition, FIG. 20 is a graph showing a relationship between the concentration of the denatured protein or the undenatured protein with respect to the sample under each condition and a reaction time till the initiation of the production of the gel particles (the axis of ordinate indicates 1/reaction time).

In Example 1, when the plasma sample was subjected to a reaction after having been diluted 100-fold, the reaction time till the initiation of the production of the gel particles became shortest and the formation of the gel particles was accelerated. Accordingly, a search for a factor for the foregoing was performed. As a result, the activity of the biological protein was not considered to play a considerable role because the heating treatment was performed as a sample treatment, and hence the possibility of the denatured protein was experimented.

According to FIG. 20, the addition of the undenatured protein did not exert a particle formation accelerating effect and only the denatured protein showed the effect. In addition, it is confirmed that none of an excessively high (2%) concentration range and an excessively low (0 or 0.0002%) concentration range is satisfactory, and a certain concentration range (1% to 0.002%) is needed for obtaining a certain effect.

In addition, it is confirmed that in the production process of the gel particles in the case where the denatured protein concentration is 0.02%, as illustrated in FIG. 18, the gel particles are produced in a state where their particle sizes are centered in a certain range. In this respect, it is confirmed that the formation of the gel particles is inhibited in the case where the denatured protein concentration is 2%, and the sizes of the produced particles are nonuniform in the case where the concentration is 0.0002% as compared with those in the case where the concentration is 0.02%.

Example 3

FIG. 21 to FIG. 24

A reagent investigating the phenomenon was domestic (manufactured by Wako Pure Chemical Industries, Ltd., LAL-ES) and subjected to various kinds of processing, and hence an effect on particle formation was reinvestigated with a reagent close to an untreated solution of a limulus reagent (CHARLES RIVER LABORATORIES (CR), Endosafe).

In Example 3, a certain amount (10 pg/ml) of an endotoxin was added to the gel particle measurement reagent manufactured by CR and then a denatured albumin (DA) as a particle formation accelerating factor was examined for its influence.

DA's having various concentrations, i.e., 1%, 0.8%, 0.4%, 0.2%, 0.1%, 0.5%, 0.02%, 0.01%, 0.001%, and 0.0001% were produced with purified albumin solutions subjected to a thermal denaturation treatment (De-A2%, De-A1%, and DeN-A1% in FIG. 24), and then reaction times till the initiation of the production of gel particles were measured by subjecting samples having the same endotoxin concentration to a reaction by the limulus reagent under the respective conditions. In addition, a distribution in each particle size of products leading to the gel particles in the production process of the gel particles under each condition was measured with a particle distribution measurement apparatus. Here, the same apparatus as that of Example 1 was used as the particle distribution measurement apparatus.

Figure 21A:
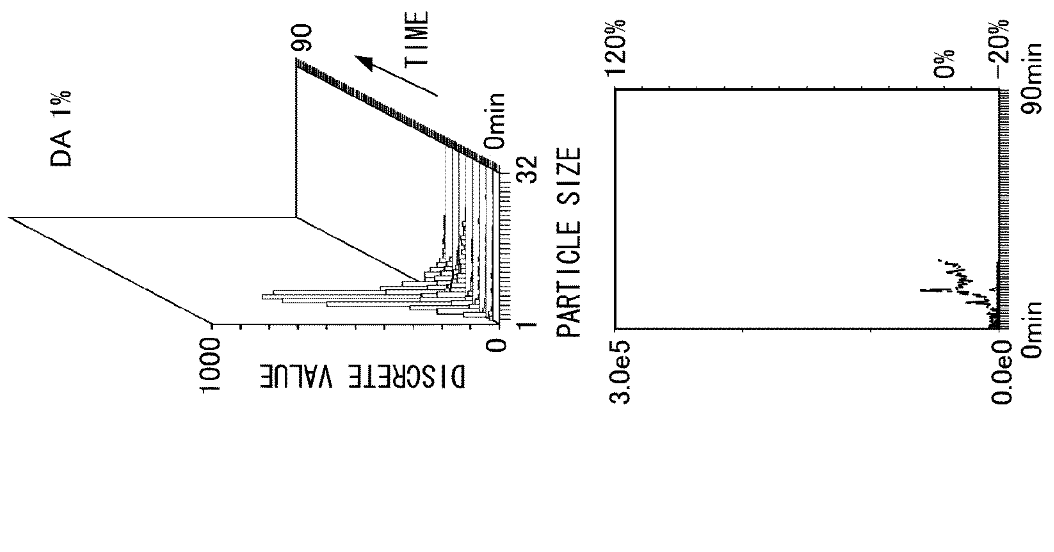
FIGS. 21A to 21C are each an explanatory diagram (1) showing the production process of gel particles to be produced when, in an embodiment in which a purified thermally denatured albumin (DA) is utilized as a particle formation accelerating factor for a sample specimen containing a certain amount (10 pg/ml) of an endotoxin in Example 3, the concentration of the DA is changed, FIG. 21A showing the case where the DA concentration is 1%, FIG. 21B showing the case where the DA concentration is 0.8%, and FIG. 21C showing the case where the DA concentration is 0.4%.
Figure 21B:
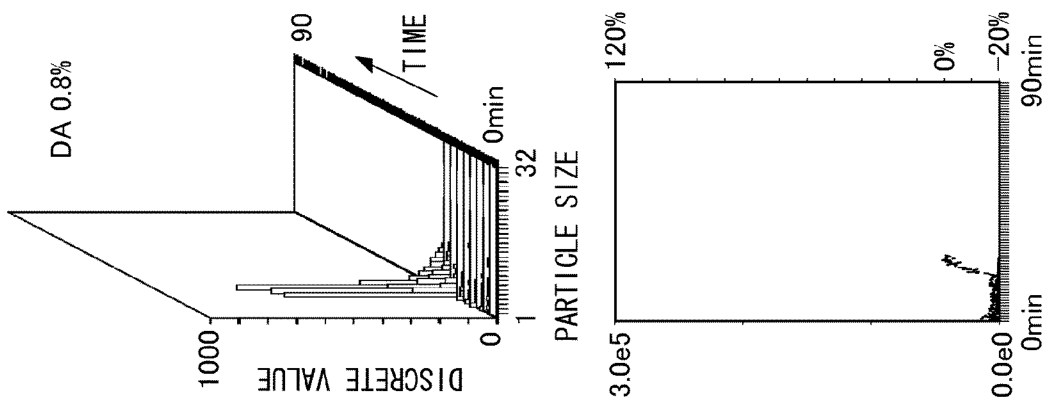
Figure 21C:
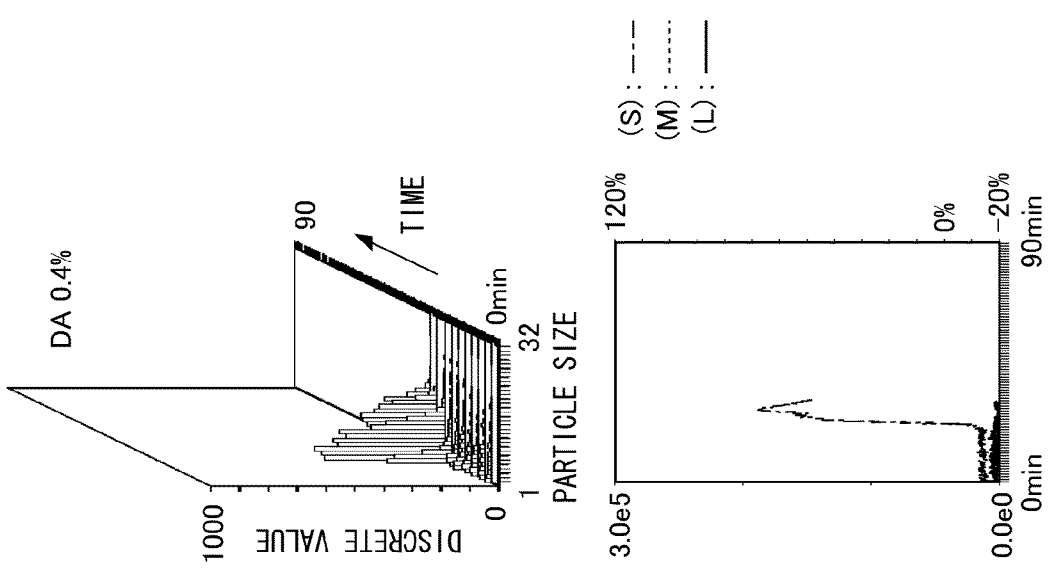
Figure 22A:
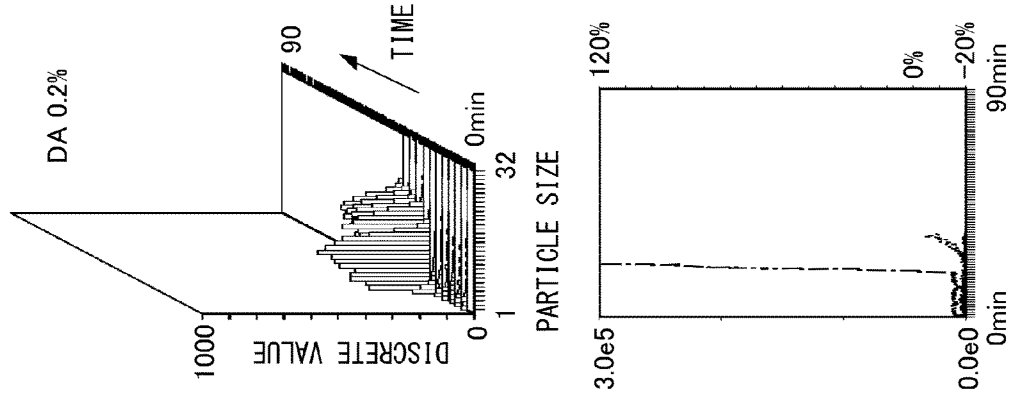
FIGS. 22A to 22C are each an explanatory diagram (2) showing the production process of the gel particles to be produced when, in the embodiment in which the purified thermally denatured albumin (DA) is utilized as a particle formation accelerating factor for the sample specimen containing a certain amount (10 pg/ml) of an endotoxin in Example 3, the concentration of the DA is changed, FIG. 22A showing the case where the DA concentration is 0.2%, FIG. 22B showing the case where the DA concentration is 0.1%, and FIG. 22C showing the case where the DA concentration is 0.05%.
Figure 22B:
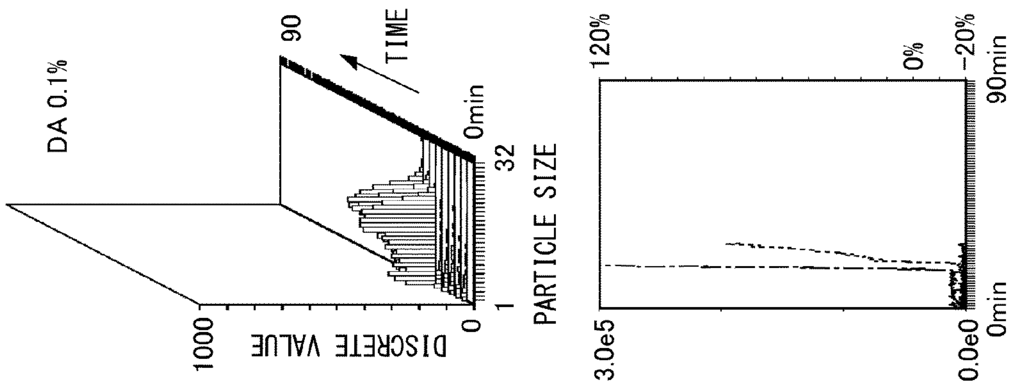
Figure 22C:
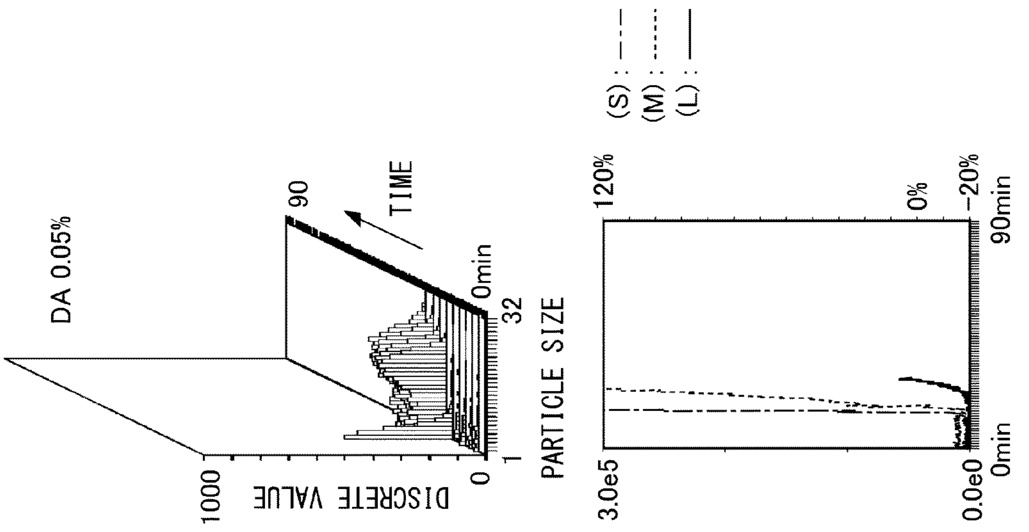

Three-dimensional graphs in the upper portions of FIG. 21 to FIG. 23 each show a situation where particles having various sizes (levels 1 to 32) are produced along a time axis, and graphs in the lower portions thereof each show the total of the numbers of particles of the upper three-dimensional graph for each of a small size (levels 1 to 15), a middle size (levels 15 to 23), and a large size (levels 24 to 32) together with an elapsed time, and each show a chronological turbidity change (-X-).

Figure 24:
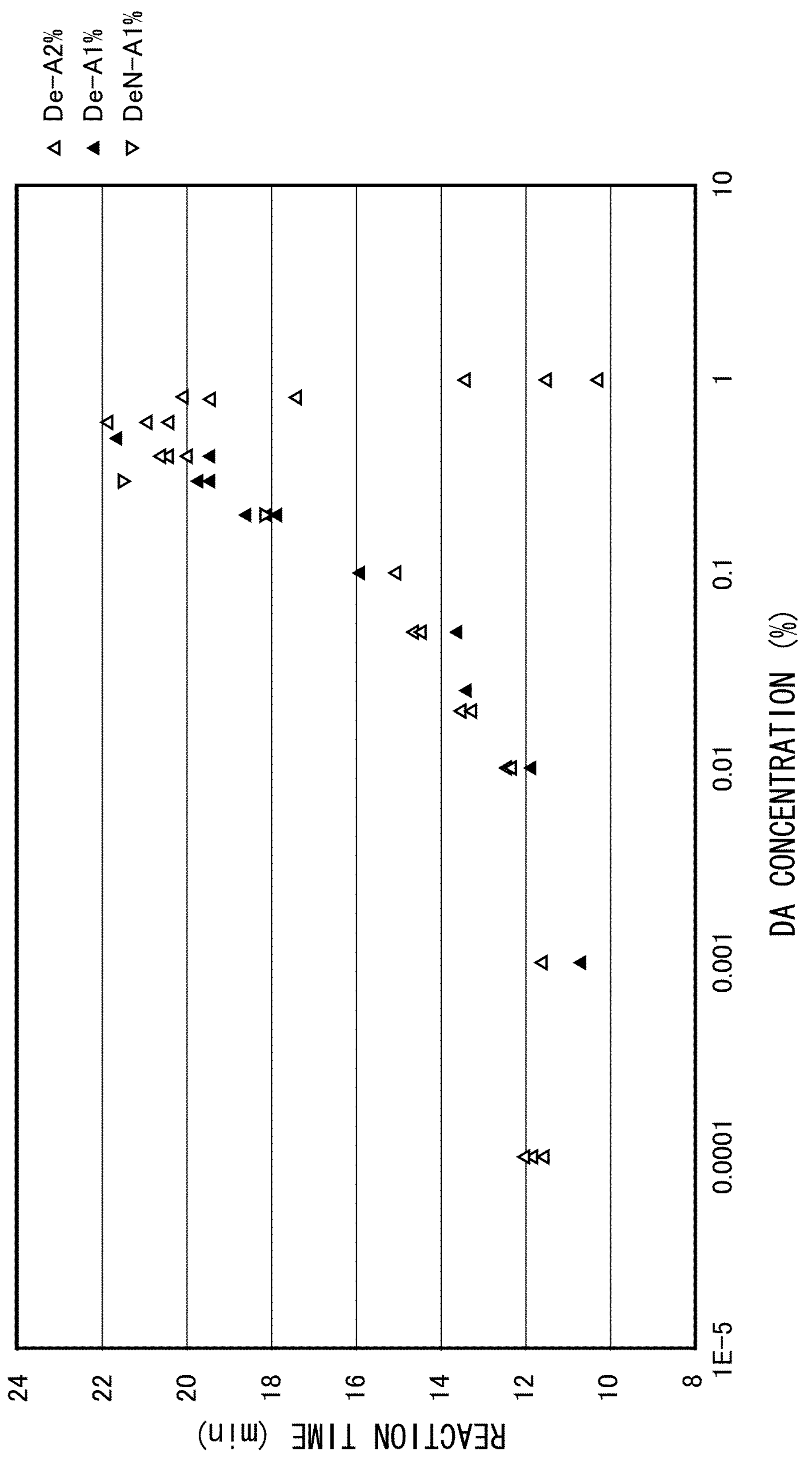
FIG. 24 is a graph chart showing a relationship between the DA concentration of Example 3 and a reaction time till the initiation of the production of the gel particles in FIG. 21 to FIG. 23.

FIG. 24 shows a relationship between the DA concentration and the reaction time till the initiation of the production of the gel particles.

Figures 23A, 23B, 23C, 23D:
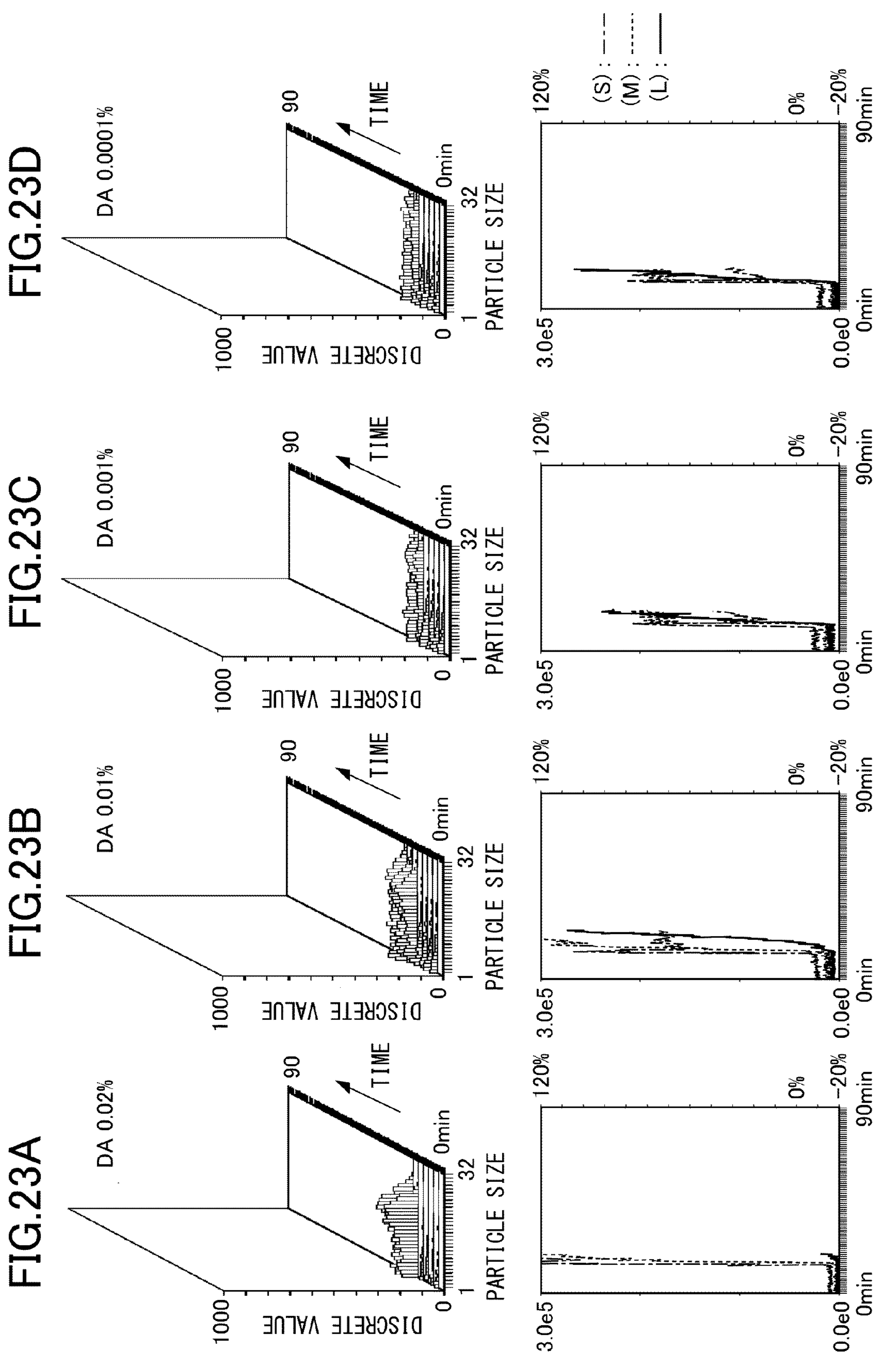
FIGS. 23A to 23D are each an explanatory diagram (3) showing the production process of the gel particles to be produced when, in the embodiment in which the purified thermally denatured albumin (DA) is utilized as a particle formation accelerating factor for the sample specimen containing a certain amount (10 pg/ml) of an endotoxin in Example 3, the concentration of the DA is changed, FIG. 23A showing the case where the DA concentration is 0.02%, FIG. 23B showing the case where the DA concentration is 0.01%, FIG. 23C showing the case where the DA concentration is 0.001%, and FIG. 23D showing the case where the DA concentration is 0.0001%.

As shown in FIG. 21 to FIG. 23, the reaction does not progress successfully when the concentration is excessively low, i.e., 0.0001% (FIG. 23D) or excessively high, i.e., 1% (FIG. 21A), and particle sizes are centered in a certain range at a concentration around 0.02% to 0.2%. That is, the particle formation was insufficient at a DA concentration of 1 to 0.8% and a nonspecific turbidity increase occurred. On the other hand, at a DA concentration of 0.01% or less, the particle formation was not controlled and particles having various sizes were formed. However, it was found that particles having a certain size were efficiently formed at a DA concentration around 0.2 to 0.02%.

FIG. 24 is obtained by plotting those appearance times (time points of the initiation of the production of the gel particles), and it is understood from the figure that the reaction time till the time point of the initiation of the production of the gel particles is short at a DA concentration around 0.02%.

It should be noted that the lowering portion on the right side of FIG. 24 results from nonspecific precipitation caused by the denatured albumin added at a high concentration, and it is apparent from, for example, FIG. 21A that the gel particles were not produced in the portion.

The foregoing results show that when the denatured albumin is present in a situation where the limulus reagent reacts with the endotoxin to form insoluble coagulin molecules but the molecules have not been formed as particles having a certain concentration yet, particles are formed with their sizes centered in a certain range. The results also show that the absence of the factor results in spontaneous formation of particles having various sizes.

That is, with regard to the detection of the gel particles on which the gel particle measurement method of this example is based, the quantitativity of the endotoxin can be secured by the following. The condition under which the coagulin molecules aggregate is kept constant, the particle formation accelerating factor is added to the reagent base material to keep the condition under which the particles are formed constant, and a method for the detection of the production of the coagulin molecules leading to the condition is kept constant.

In addition, the plasma sample showed an optimum concentration around 1%. However, in consideration of the concentration of the plasma protein in blood and the concentration of its active component, the effective concentration is one tenth to one ten severalth or less of the optimum concentration, and hence may substantially coincide with a concentration of 0.2 to 0.02% obtained from the verification experiment using a pure protein. However, the protein concentration of a plasma sample varies depending on, for example, the condition of a patient, and measuring objects such as the endotoxin include a sample free of any protein like a dialysate to be used in artificial dialysis. As long as the gel particle formation is the basic principle of the measurement method, the production of a limulus reagent to which a specific particle formation accelerating factor corresponding to the optimum concentration range has been added in advance is an indispensable condition in a sense that stable quantitative determination conditions are secured in those samples.

<Structure of Denatured Albumin>

Figure 25:
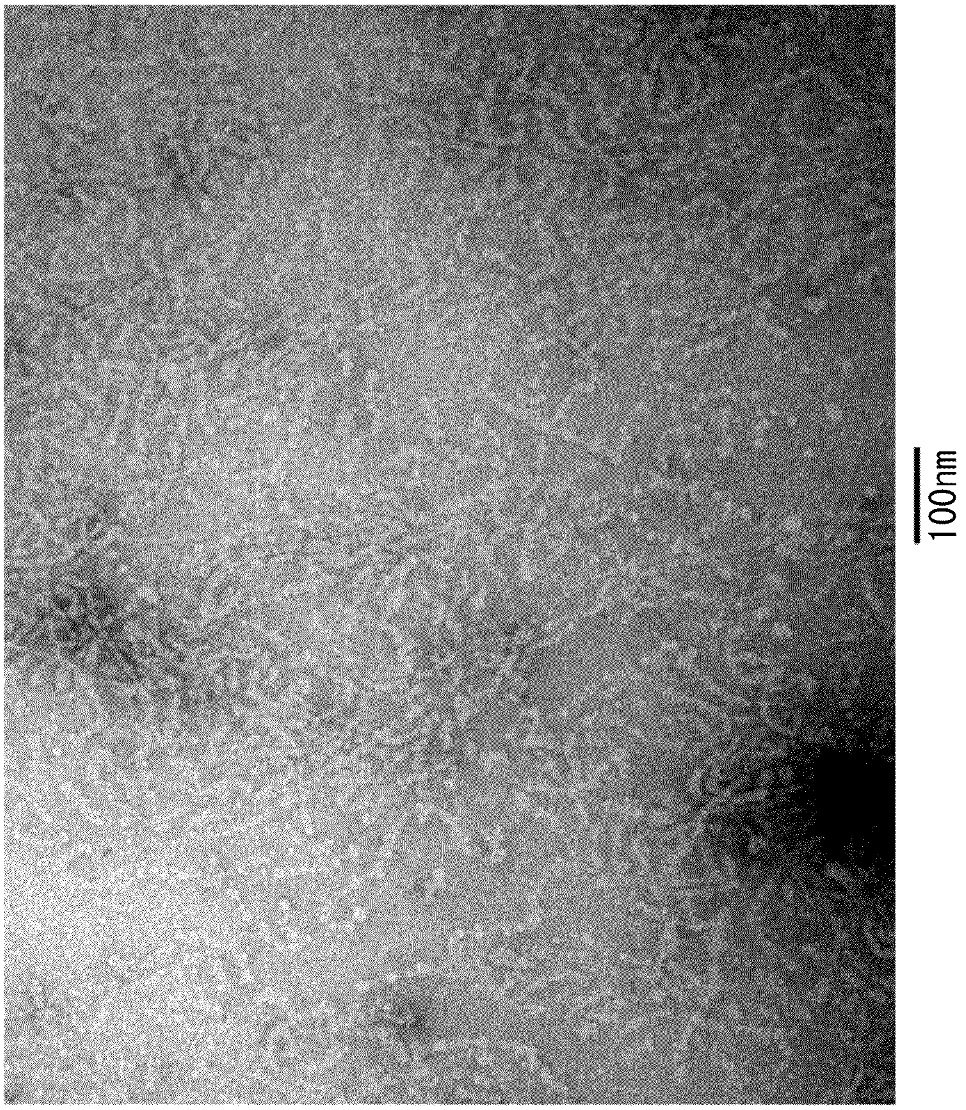
FIG. 25 is an explanatory diagram showing the structure of the denatured albumin as a particle formation accelerating factor utilized in Example 3 observed with an electron microscope.

In order for the structure of the "denatured albumin" used as the particle formation accelerating factor in Example 3 to be examined, the negative staining of a soluble denatured albumin (undiluted solution: 1% (v/v)) was performed. FIG. 25 shows a transmission electron microscope photograph for the negative staining.

According to the figure, it was confirmed that a plurality of albumins denatured by being subjected to thermal denaturation gathered to form a thin, fibrous structure. With regard to its sizes, the fibrous structure had a diameter dimension of about 10 nm and a length of fifty to several hundred nanometers.

It should be noted that an undenatured albumin is a protein having a molecular weight of about 50,000, and even the employment of the negative staining does not enable the observation of any fibrous structure, though a spherical lump structure is observed.

<Role of Denatured Albumin>

In consideration of the result of the observation shown in FIG. 25 and the fact that the optimum concentration of the particle formation accelerating factor is present in the range of 0.002% to 1%, a role played by the fibrous denatured albumin as a condition under which the coagulin molecules aggregate upon production of the gel particles is assumed to be as follows: the albumin serves as a core (or seed) to which the coagulin molecules cling.

Figures 26A, 26B, 26C:
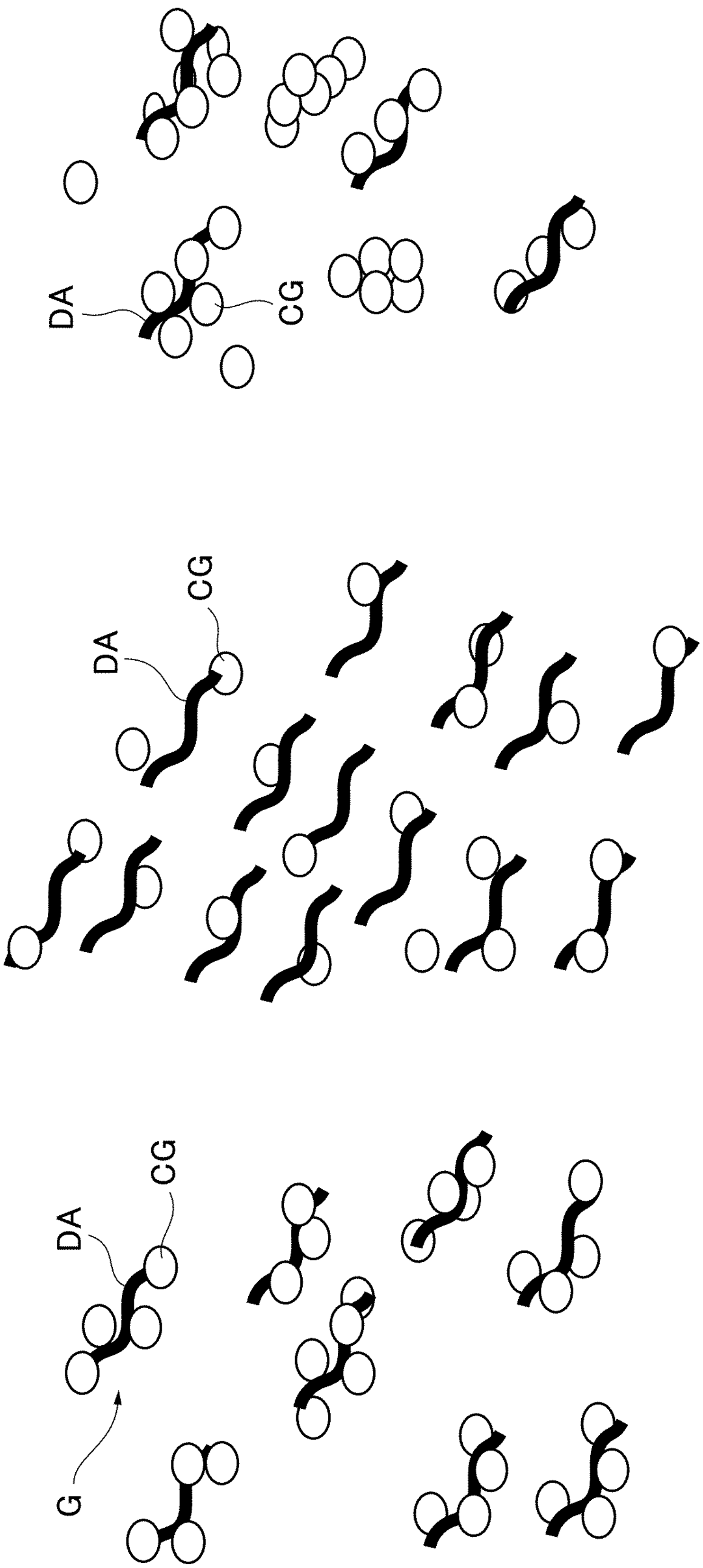
FIGS. 26 A to 26C are each an explanatory diagram schematically illustrating a role played by the denatured albumin in the production process of the gel particles.

In other words, as illustrated in FIG. 26A, as long as the concentration of the denatured albumin DA falls within an optimum range, coagulin molecules CG that have gone critical appropriately aggregate to be formed as an aggregate grown to a proper size (corresponding to the gel particle G that is being observed). However, when the amount of the denatured albumin DA serving as a core is excessively large, as illustrated in FIG. 26B, the coagulin molecules CG are dispersed and hence a large aggregate cannot be formed. In addition, when the amount of the denatured albumin DA serving as a core is excessively small, as illustrated in FIG. 26C, an aggregate having a certain size cannot be formed, which may lead to the need for an extra time for the formation of the observable gel particle G.

Example 4

In this example, an experiment substantially identical to that of Example 3 was performed with particle formation accelerating factors different from the denatured protein (denatured albumin) as the particle formation accelerating factor used in Example 3.

In this example, the following materials were each used as the particle formation accelerating factor.

Denatured protein except denatured albumin
Cellulose
Polysaccharide
Glycoprotein Each particle formation accelerating factor was added to a reagent close to an undiluted solution of a limulus reagent (CHARLES RIVER LABORATORIES (CR), Endosafe) at a predetermined concentration, and then an effect on particle formation was investigated in a state where the resultant was stirred and mixed with a solution containing an endotoxin. As a result, a tendency substantially identical to that of Example 3 (a good result for a product to which the particle formation accelerating factor was added at a concentration of 0.002% to 1%) was observed.

It should be noted that when the same experiment was performed on a nanoparticle resin as any other particle formation accelerating factor with, for example, a fullerene (cage-like carbon fiber), a tendency substantially identical to that of the other particle formation accelerating factor described in the foregoing was observed.

The foregoing corroborates that the particle formation accelerating factor is not limited to denatured proteins typified by a denatured albumin, and biogenic polymer fine particles such as celluloses, polysaccharides, and glycoproteins, and petroleum polymer chemical component-derived porous fine particles such as a nanoparticle resin each also act in substantially the same manner.

INDUSTRIAL APPLICABILITY

The present invention is widely applied to a measurement apparatus in which a target substance capable of producing gel particles through a gelation reaction is to be measured, as well as a gel particle measurement apparatus in which an endotoxin or a β-D-glucan is to be measured using a limulus reagent.

For example, the present invention can be applied to a blood-clotting reaction or an antigen-antibody reaction.

Figure 27:
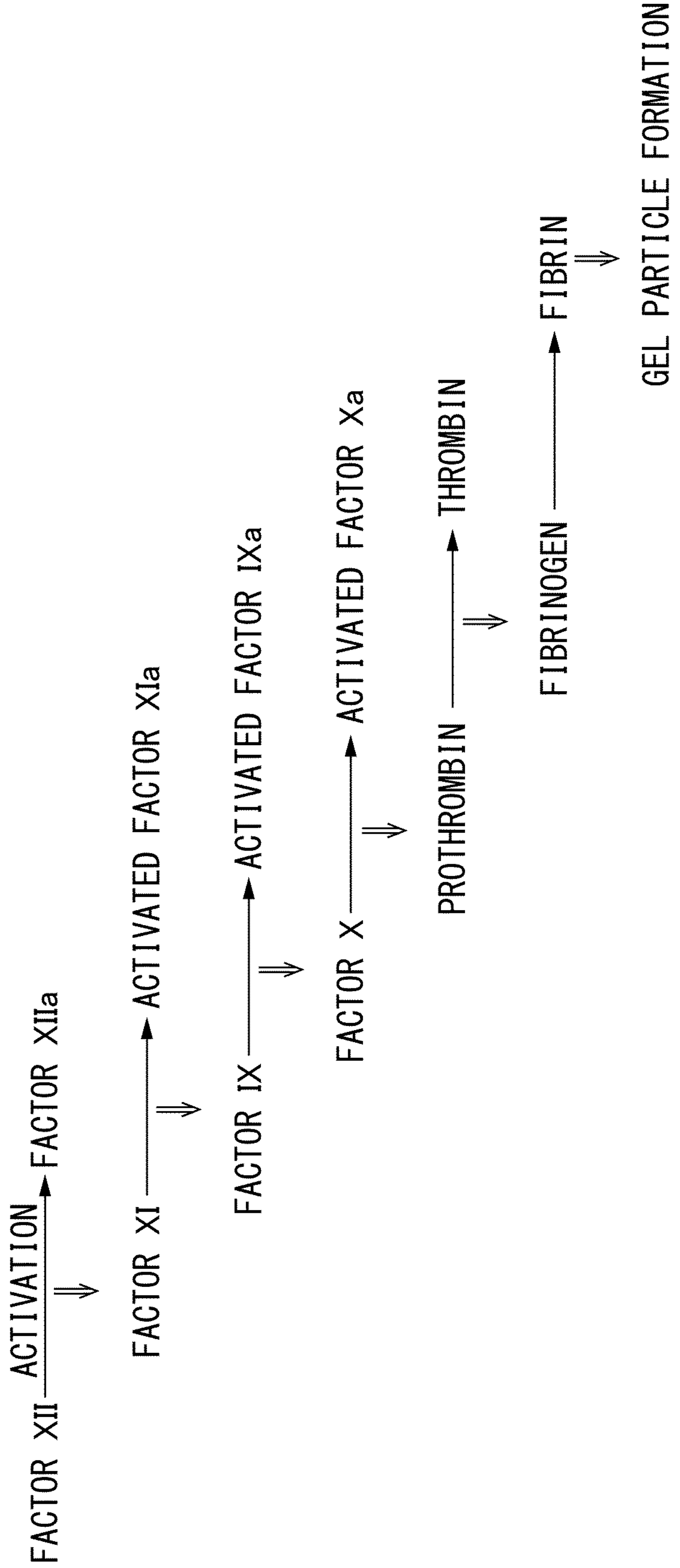
FIG. 27 is an explanatory diagram illustrating an application example of the present invention in a blood-clotting reaction.

—Blood-Clotting Reaction (FIG. 27)—

Prothrombin in plasma becomes thrombin through activation of various blood-clotting factors, and fibrin aggregates.

When a supplemental description is made of the foregoing, a coagulation system of plasma progresses through an initiation period, an amplification period, and a propagation period shown below.

<Initiation Period>

(Extrinsic Pathway)

When a cell is damaged in a blood-clotting cascade, a tissue factor binds to factor VIIa (activated factor VII).

In this case, factor VIIa activates factor IX to produce factor IXa. Further, factor IXa activates factor X to produce factor Xa.

(Intrinsic Pathway)

When blood comes into contact with a solid (for example, rock or sand) charged negatively, prekallikrein and a high-molecular-weight kininogen activate factor XII to produce factor XIIa. Further, factor XIIa activates factor XI to produce factor XIa. Further, factor XIa activates factor IX to produce factor IXa.

(Amplification Period)

Thrombin activates factor XI to produce factor XIa. Factor XIa activates factor IX to produce factor IXa. Further, thrombin itself activates factor V and factor VIII to produce factor Va and factor VIIIa, respectively. Further, thrombin activates platelet to bind factor XIa, factor Va, and factor VIIIa to the surface of platelet.

(Propagation Period)

Factor VIIIa and factor IXa bound to the surface of platelet activate factor X to be bound to the surface of platelet. Further, factor Xa and factor XIa bound to the surface of platelet change prothrombin to thrombin successively. Further, a large amount of thrombin decomposes fibrinogen in plasma to produce a fibrin monomer. The fibrin monomer is cross-linked with factor XIII to produce a fibrin polymer, which involves other blood cells to become a blood clot (scab).

In a living body, the above-mentioned reaction is useful for closing the wound through blood clotting, for example. However, on the other hand, when a minute aggregate is generated in blood stream, the clot becomes a blood clot to close various small blood vessels to cause serious clinical conditions such as brain ischemia, cardiac ischemia, and pulmonary embolism. Thus, the clinical determination of "ease of aggregation" is important for predicting the generation of an aggregate. Hitherto, a prolonged aggregation time has been measured based on the fear that "bleeding does not stop." However, there is no estimated method of measuring "ease of blood clotting." It is expected that the degree of aggregation can be measured by mixing plasma diluted appropriately and a certain amount of a reagent (for example, ADP, collagen, or epinephrine) for accelerating aggregation through the particle measurement method.

Therefore, in this example, a certain amount of ADP or the like is placed aseptically in the sample cuvet 100 together with the magnetic stirrer bar 121 to prepare the sample cuvet 100 subjected to treatment such as freeze drying. Plasma diluted appropriately in clinical practice is introduced into the sample cuvet 100 through the sealing stopper 108 in the upper part, and a time till the production of an aggregate, that is, a time till the initiation of gelation is measured with a gel particle measurement apparatus similar to that of the first embodiment. Thus, the degree of an aggregation ability can be measured.

—Antigen-Antibody Reaction (FIG. 28)—

Figure 28A:
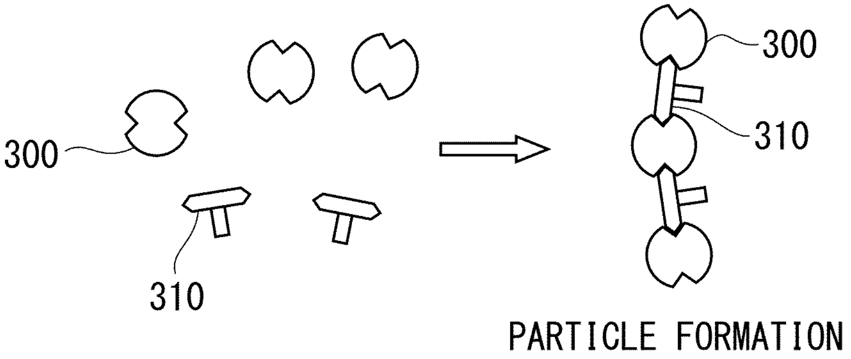
FIGS. 28A and 28B are each an explanatory diagram illustrating an application example of the present invention in an antigen-antibody reaction.

As illustrated in FIG. 28A, specific antibodies 310 against various antigens 300 associate to accelerate the inactivation of the antigens 300 as insoluble precipitates and defend a living body. Meanwhile, when the specific antibodies 310 are prepared in advance, the amount of precipitates to be produced is proportional to that of the antigens 300 that are present, and hence various methods of quantifying the antigens 300 have been devised through use of the above-mentioned phenomenon. However, it takes a long time for precipitation (or accelerating the antigen-antibody association), and hence, various detection methods and sensitive detection apparatus have been developed. When the precipitate formation in an antigen-antibody reaction is taken as particle formation of gelation, a gel particle measurement apparatus for forming particles stably and measuring the particles is considered to be applicable.

Figure 28B:
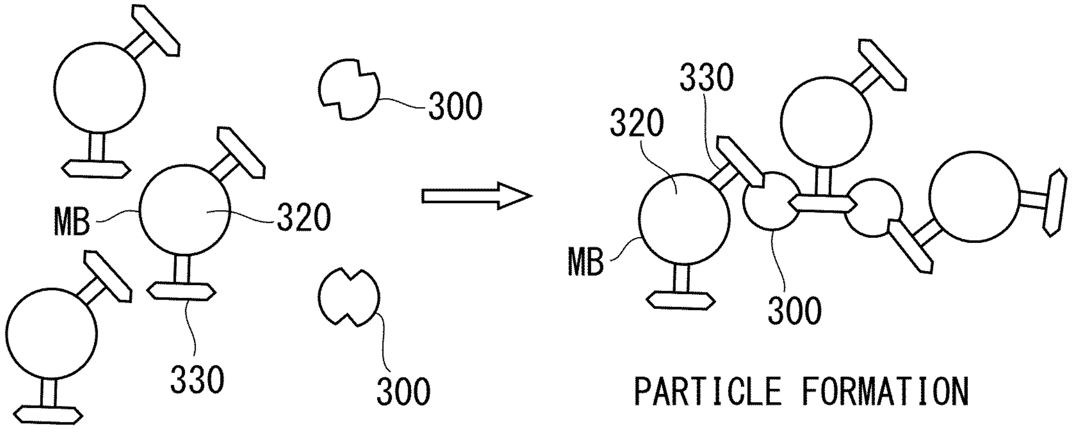

Above all, as illustrated in FIG. 28B, in a detection reaction of a type involving binding the antibodies 330 to microbeads (MB) 320 or the like made of a resin or the like and causing an antigen-antibody reaction to occur between the surface of the beads and the antigen 300, the precipitate formation can be easily found by a change in pattern of particle formation, and this can also be applied to the method.

Therefore, a certain amount of the antibody 330 or a solution of the antibody bound to the microbeads 320 is placed aseptically in the sample cuvet 100 together with the magnetic stirrer bar 121. In this case, it is necessary to keep the activity of the antibody 330, and hence it is considered to be better to preserve the antibody 330 as a solution instead of a freeze-dried state. In the case of performing measurement, an analyte solution such as plasma diluted in a predetermined manner is introduced into the sample cuvet 100 through the sealing stopper 108 in the upper part, and the production rate of aggregates by the antigen-antibody reaction is measured, for example, with the gel particle measurement apparatus of the first embodiment. In particular, a reduction rate of transmitted light is measured so as to grasp the production rate of gel particles.

The methods of using the following three reactions: an endotoxin active reaction, a blood-clotting reaction, and an antigen-antibody reaction described in the first embodiment are common in grasping a reaction in which molecules dissolved homogeneously in water associate to become insoluble particles and quantitatively determining the particles. When the soluble molecules become insoluble, a reaction bias (reaction molecules are locally insufficient around an enzyme to be the center of the reaction) phenomenon occurs. In order to allow the reaction to progress correctly and measure the rate thereof, this bias needs to be "zero" theoretically. A solution to the problem is "stirring." The measurement method mainly involves stirring a solution homogeneously and allowing particles to be formed stably.

REFERENCE SIGNS LIST

1 . . . reagent base material, 2 . . . particle formation accelerating factor, 3 . . . sample cuvet, 4 . . . stirring device, 5 . . . incident light source, 6 . . . detection device, G . . . gel particle, S . . . sample, R . . . reagent, W . . . mixing solution, Bm . . . light.

The invention claimed is:

1. A gel particle measurement reagent capable of being used to be agitated continuously with a sample containing a target substance as a measuring object to turn the target substance into gel particles, comprising:

a reagent base material that undergoes a gelation reaction with the target substance; and a particle formation accelerating factor that is added to the reagent base material, has biological inactivity and solubility in the sample and dissolves therein at a concentration of 0.002 to 1%, and accelerates production of gel particles whose particle sizes are centered in a predetermined range by accelerating the aggregation of products leading to the gel particles; and the reagent base material and the particle formation accelerating factor are capable of being used under conditions in which a mixing solution is subject to a continuously agitating state to inhibit the gelation of the entire mixing solution.

2. A gel particle measurement reagent according to claim 1, wherein the particle formation accelerating factor comprises a soluble, thermally denatured protein.

3. A gel particle measurement reagent according to claim 1, wherein the particle formation accelerating factor is a soluble, inactive, biogenic polymer fine particle or a petroleum polymer chemical component-derived porous fine particle.

4. A gel particle measurement reagent according to any one of claims 1 to 3, wherein:

the target substance as the measuring object is an endotoxin or a β-D-glucan; and the reagent base material comprises a limulus reagent.

5. A gel particle measurement method of measuring a target substance in a sample turned into particles by a gelation reaction under agitated condition, the method comprising:

storing, in a sample cuvette at least partially having an incident portion through which light enters and an exit portion through which the light exits, a sample containing the target substance as a measuring object and a solution containing the gel particle measurement reagent according to any one of claims 1 to 3 causing gelation of the target substance;

stirring continuously a mixing solution formed of the sample and the solution of the reagent in the sample cuvette with stirring device to suppress gelation of an entirety of the mixing solution;

irradiating, which is performed in parallel to the stirring step, the agitating solution formed of the sample and the solution of the reagent in the sample cuvette with coherent light from an incident light source provided outside the incident portion of the sample cuvette;

detecting, which is performed in parallel to the stirring step, a light component scattered from or transmitted through gel particles to be produced in the agitating solution formed of the sample and the solution of the reagent in the sample cuvette at a time point at which the agitating solution undergoes a phase transition from a sol phase to a gel phase with detection device provided outside the exit portion of the sample cuvette; and determining a time point of initiation of the production of the gel particles in the agitating solution based on a detection output obtained in the detecting step.

6. The gel particle measurement reagent according to claim 1, wherein the particle formation accelerating factor accelerates production of gel particles whose particle sizes are centered in a range biased to small sizes by accelerating the aggregation of products leading to the gel particles.

7. The gel particle measurement method according to claim 5, wherein the detecting step detects a scattered light component returning to the rear of the incident light source in a light component scattered from or transmitted through gel particles to be produced in the agitating solution formed of the sample and the solution of the reagent in the sample cuvette.

8. The gel particle measurement reagent according to claim 1, wherein the particle formation accelerating factor has a concentration of 0.02 to 0.2%.

9. The gel particle measurement reagent according to claim 8, wherein the particle formation accelerating factor is thermally denatured albumin.

10. The gel particle measurement reagent according to claim 1, wherein the particle formation accelerating factor is added to the reagent base material which in advance is constituted so as to be of a freeze-dried powder shape.

11. The gel particle measurement reagent according to claim 1, wherein the particle formation accelerating factor is contained to a diluent which is provided separately from the reagent base material of a freeze-dried powder shape.

* * * * *